US009089598B2

(12) United States Patent
Luyten et al.

(10) Patent No.: US 9,089,598 B2
(45) Date of Patent: Jul. 28, 2015

(54) METHOD OF TREATING CONNECTIVE TISSUE DEFECT USING CHONDROCYTES SELECTED FOR PHENOTYPIC STABILITY

(75) Inventors: Frank Luyten, Kraainem (BE); Cosimo De Bari, Aberdeen (GB); Francesco Dell'Accio, Bromley (GB)

(73) Assignee: TIGENIX N.V., Leuven (BE)

( * ) Notice: Subject to any disclaimer, the term of this patent is extended or adjusted under 35 U.S.C. 154(b) by 863 days.

(21) Appl. No.: 12/323,185

(22) Filed: Nov. 25, 2008

(65) Prior Publication Data

US 2009/0162328 A1 Jun. 25, 2009

Related U.S. Application Data

(62) Division of application No. 10/089,932, filed as application No. PCT/BE00/00118 on Oct. 6, 2000, now Pat. No. 7,479,367.

(30) Foreign Application Priority Data

Oct. 6, 1999 (EP) ..................................... 99203273

(51) Int. Cl.
*C12N 5/00* (2006.01)
*A61K 49/00* (2006.01)
(52) U.S. Cl.
CPC .......... *A61K 49/0006* (2013.01); *A61K 49/0004* (2013.01); *A61K 49/0008* (2013.01); *Y10S 435/975* (2013.01)
(58) Field of Classification Search
None
See application file for complete search history.

(56) References Cited

U.S. PATENT DOCUMENTS

| 5,723,331 | A | 3/1998 | Tubo |
| 5,837,258 | A | 11/1998 | Grotendorst |
| 5,902,785 | A | 5/1999 | Hattersley |
| 2003/0235813 | A1 | 12/2003 | Luyten |

FOREIGN PATENT DOCUMENTS

| WO | WO 96/41620 | 12/1996 |
| WO | WO 98/53103 | 11/1998 |
| WO | WO 98/59035 | 12/1998 |
| WO | WO 01/24833 | 4/2001 |
| WO | WO 01/25402 | 4/2001 |

OTHER PUBLICATIONS

Office Action for European Patent Application No. 04 077 642.9, dated Jun. 25, 2009.
Office Action for Canadian Patent Application No. 2,397,610, dated Aug. 27, 2010.
Binette et al., "Expression of a Stable Articular Cartilage Phenotype without Evidence of Hypertrophy by Adult Human Articular Chondrocytes in Vitro," *J. Orthop. Res.* 16(2): 207-216 (1998).
Bradham and Horton "In Vivo Cartilage Formation from Growth Factor Modulated Articular Chondrocytes," *Clin. Orthop. Relat. Res.* (352):239-249 (1998).
Erlacher et al., "Cartilage-Derived Morphogenetic Proteins and Osteogenic Protein-1 Differentially Regulate Osteogenesis," *J. Bone Miner. Res.* 13(3):383-392 (1998).
Hamada et al., "Immunohistochemical Localization of Fibroblast Growth Factor Receptors in the Rat Mandibular Condylar Cartilage and Tibial Cartilage," *J. Bone Miner. Metab.* 17(4):274-282 (1999).
U.S. Appl. No. 10/089,932, filed Jul. 29, 2002, Luyten.
Kolettas et al., "Expression of Cartilage-Specific Molecules is Retained on Long-Term Culture of Human Articular Chondrocytes," *J. Cell Sci.* 108(Pt. 5):1991-1999 (1995).
Meyer et al., "Mapping the Type I Collagen-Binding Site on Pigment Epithelium-Derived Factor. Implications for its Antiangiogenic Activity," *J. Biol. Chem.* 277(47):45400-45407 (2002).
Quan et al., "Localization of Pigment Epithelium-Derived Factor in Growing Mouse Bone," *Calcif. Tissue Int.* 76(2):146-153 (2005.).
Quarto et al., "Modulation of Commitment, Proliferation, and Differentiation of Chondrogenic Cells in Defined Culture Medium," *Endocrinology* 138(11):4966-4976 (1997).
Rousseau et al., "Mutations in the Gene Encoding Fibroblast Growth Factor Receptor-3 in Achondroplasia," *Nature* 371(6494):252-254 (1994).
Schumacher et al., "Immunodetection and Partial cDNA Sequence of the Proteoglycan Superficial Zone Protein, Synthesized by Cells Lining Synovial Joints," *J. Orthop. Res.* 17(1):110-120 (1999).
Si et al., "Expression of BMP-2 and TGF-beta 1 mRNA During Healing of the Rabbit Mandible," *Eur. J. Oral Sci.* 105(4):325-330 (1997) (Abstract only).
Stewart et al., "Phenotypic Stability of Articular Chondrocytes in Vitro: The Effects of Culture Models, Bone Morphogenetic Protein 2, and Serum Supplementation," *J. Bone Miner. Res.* 15(1):166-174 (2000).
Valcourt et al., "Different Effects of Bone Morphogenetic Proteins 2, 4, 12, and 13 on the Expression of Cartilage and Bone Markers in the MC615 Chondrocyte Cell Line," *Exp. Cell Res.* 251(2):264-274 (1999).

(Continued)

*Primary Examiner* — Blaine Lankford
(74) *Attorney, Agent, or Firm* — Clark & Elbing LLP

(57) ABSTRACT

An in vivo assay to measure anchorage-independent growth and phenotypic stability of a certain cell population comprising subcutaneous or intramuscular injection in a mammal of a cell suspension of articular chondrocytes in an iso-osmotic liquid, the same suspension comprising articular chondrocytes in an amount equivalent to at least $1 \times 10^6$ chondrocytes as applied to immune-deficient mice. The outcome is linked to molecular markers. The present invention further relates to DNA chips and diagnostic tools comprising the latter to predict the outcome of ACT. Antibodies raised against positive and negative markers of chondrocyte stability can also be used for quality control on the chondrocytes. Therapeutical composition comprising stable chondrocytes are very useful for tissue repair.

3 Claims, 9 Drawing Sheets

(56) References Cited

OTHER PUBLICATIONS

Office Action for U.S. Appl. No. 10/089,932 (dated Oct. 5, 2004).
Office Action for U.S. Appl. No. 10/089,932 (Apr. 21, 2006).
Office Action for U.S. Appl. No. 10/089,932 (dated Oct. 24, 2006).
Office Action for U.S. Appl. No. 10/089,932 (dated Apr. 19, 2007).
Office Action for U.S. Appl. No. 10/089,932 (dated Jan. 14, 2008).
Notice of Allowance for U.S. Appl. No. 10/089,932 (dated Aug. 22, 2008).
Office Action for U.S. Appl. No. 10/422,475 (dated Sep. 30, 2004).
Office Action for U.S. Appl. No. 10/422,475 (dated Apr. 21, 2006).
Office Action for U.S. Appl. No. 10/422,475 (dated Oct. 18, 2006).
Office Action for U.S. Appl. No. 10/422,475 (dated May 31, 2007).
Office Action for U.S. Appl. No. 10/422,475 (dated Dec. 4, 2007).
Notice of Allowance for U.S. Appl. No. 10/422,475 (dated Sep. 9, 2008).

METHOD OF TREATING CONNECTIVE TISSUE DEFECT USING CHONDROCYTES SELECTED FOR PHENOTYPIC STABILITY

CROSS-REFERENCE TO RELATED APPLICATIONS

This application is a divisional of U.S. application Ser. No. 10/089,932, filed on Jul. 29, 2002, which is the U.S. National Stage of International Application No. PCT/BE00/00118, filed Oct. 6, 2000, which claims the benefit of European Application No. 9203273.0, filed Oct. 6, 1999.

The present invention relates to the field of cartilage repair in general, and more specifically to the generation of an optimal cell population suitable for the repair of joint surface defects and the repair of the cartilage skeleton in general.

BACKGROUND OF THE INVENTION

Cartilage is a tissue composed by a cellular component, chondrocytes, and by an extra-cellular matrix typically rich in collagen type II and highly sulphated high molecular weight proteoglycan aggregates. The latter property confers cartilage its peculiar histochemical characteristics that are: strong staining with Alcian blue at low pH (from 0.2 to 2.5) and metachromacy with Toluidine blue and Safranin O. The abundance of type II collagen, link protein, and proteoglycan aggrecan, along with the presence of minor collagens such as type IX and type XI collagen are hallmarks of cartilage tissue.

In post-natal mammals, cartilage contributes to the structure of several organs and systems like the articular surface of diarthrodial joints and other joint-associated structures (such as menisci), the ear, the nose, the larynx, the trachea, the bronchi, structures of the heart valves, part of the costae, synchondroses, entheses etc. In some of the mentioned locations (e.g. entheses, the annulus fibrosus of the intervertebral disks, in the menisci, insertion of ligaments etc.) for the abundance of collagens (mostly type I collagen) and the peculiar distribution of the fibrous bundles it is called fibrocartilage. In other locations (e.g. the pinna of the ear, epiglottis etc.) it is particularly rich of elastin and it is called elastic cartilage. In all the other structures, for its semi-transparent, clear aspect it is called hyaline cartilage.

During embryogenesis cartilage has a role in the development of long bones. Mesenchymal cells aggregate and differentiate to form cartilage anlagen, which provide the mold of the future long bones. These cartilage templates in development evolve, undergo endochondral bone formation through a cascade of events including chondrocyte hypertrophy, vascular invasion, mineralization, and are eventually replaced by bone except for a thin layer at the extremities of the bone elements that will differentiate into the articular surface of diarthrodial joints. In these locations cartilage tissue remains hyaline for all the life-span of the individual. With ageing, articular cartilage is well known to undergo a process of senescence, affecting its mechanical properties and its intrinsic resilience.

Joint surface defects can be the result of various aetiologies such as inflammatory processes, neoplasias, post-traumatic and degenerative events etc. Whatever the cause, the mechanisms of repair and of subsequent evolution are largely common.

Osteochondral (or full-thickness) articular surface defects include damage to the articular cartilage, the underlying subchondral bone tissue, and the calcified layer of cartilage located between the articular cartilage and the subchondral bone. They typically arise during severe trauma of the joint or during the late stages of degenerative joint diseases, e.g. during osteoarthritis. These lesions disrupt the congruence between the joint surfaces and therefore can lead to OA, which can be painful and severely limit the joint function. Osteochondral defects can rely on an extrinsic mechanism for repair. Extrinsic healing uses mesenchymal elements from subchondral bone to participate in the formation of new connective tissue. The repair tissue, however, often consists of fibrocartilage or fibrous tissue. This scar tissue does not share the same biomechanical properties as hyaline cartilage and eventually degenerates with the development of osteoarthritis.

Superficial or partial-thickness injuries of the articular cartilage that do not penetrate the subchondral bone can only rely on an intrinsic mechanism for repair. Chondrocytes adjacent to the injured surfaces proliferate and increase the deposition of extracellular materix synthesis. Despite these attempts at repair, there is no appreciable increase in the bulk of cartilage matrix and the repair process is rarely effective in healing the defects. Although initially sometimes painless, partial-thickness defects often degenerate into osteoarthritis of the involved joint.

Repair of articular cartilage defects with suspensions of chondrocytes has been carried out in a variety of animal models (Brittberg et al. (1996) Clin. Orthop. (326):270-83) and is now employed in humans (Brittberg et al. N Engl J Med. 1994 Oct. 6; 331(14):889-95). Autologous chondrocytes obtained from an unaffected area of the joint are released, expanded in vitro in the presence of autologous serum and subsequently injected under a periosteal flap sutured to cover the cartilage defect. This procedure has led to a proven at least symptomatic amelioration. This conceptually promising approach has still wide margins for improvement, since it is known that in vitro expansion of chondrocytes results, after a limited number of cell divisions, in a loss of their phenotypic stability (as defined by the ability of chondrocytes to form hyaline cartilage in vivo) making the cell suspension to be injected unreliable.

Three alternative approaches have been developed in an attempt to improve the success rate in treating mammalian articular cartilage defects. In the first approach, synthetic carrier matrices are impregnated with allogeneic chondrocytes and then implanted into the cartilage defect where they hopefully produce and secrete components of the extracellular matrix to form articular cartilage at the site of the defect. A variety of synthetic carrier matrices have been used to date and include three-dimensional collagen gels (e.g. U.S. Pat. No. 4,846,835), reconstituted fibrin-thrombin gels (e.g. U.S. Pat. Nos. 4,642,120; 5,053,050 and 4,904,259), synthetic polymer matrices containing polyanhydride, polyorthoester, polyglycolic acid and copolymers thereof (U.S. Pat. No. 5,041,138), and hyaluronic acid-based polymers. Once a mitotically expanded population of chondrocytes is obtained, the cells can be implanted either back into the same subject from which their parent cells were originally derived (autologous implantation), or into a different subject (heterologous implantation). In addition, heterologous implantation may use chondrocytes obtained from a related or unrelated individual of the same species (allogeneic), or from a different species (xenogeneic). Alternatively, chondrocytes may be obtained from an established, long-term cell line that is either allogeneic or xenogeneic.

The introduction of non-autologous materials into a patient, however, may stimulate an undesirable immune response directed against the implanted material, leading to potential rejection of the newly-formed and engrafted cartilage tissue. In addition, heterologous implantation risks the transmission to the subject of infectious agent(s) present in the tissue or cell line. Neo-cartilage may be formed around the periphery of the implant thereby preventing integration of the implant into the cartilage defect. Monitoring the formation and development of the resulting synthetic cartilage in situ is difficult to perform and usually involves an arthroscopic or open joint examination. Furthermore, implants containing synthetic polymer components may be unsuitable for repairing large cartilage defects since polymer hydrolysis in situ inhibits the formation of cartilage and/or its integration into the defect.

In the second approach, the defect is filled with a biocompatible, biodegradable matrix containing chemotactic and mitogenic growth factors to stimulate the influx of chondrocyte progenitor cells into the matrix in situ. The matrices optimally contain pores of sufficient dimensions to permit the influx into, and proliferation of the chondrocyte progenitor within the matrix. The matrix also may contain differentiating growth factors to stimulate the differentiation of chondrocyte progenitor cells into chondrocytes which in turn hopefully secrete extracellular matrix components to form cartilage at the site of the defect in situ (e.g. U.S. Pat. Nos. 5,206,023 and 5,270,300 and EP-A-530,804). This approach however results in problems similar to those associated with the first approach hereinabove. Furthermore there is no data so far that articular cartilage contains chondrocytic progenitors available for partial thickness defect repair.

In the third approach, chondrocytes may be cultured and expanded in vitro thereby to form synthetic cartilage-like material that is implanted subsequently into the cartilage defect. This has the advantage over the previous methods in that the development of the synthetic cartilage material may be monitored, through morphological, biochemical, and molecular characterisation, prior to implantation. Chondrogenic cells may be expanded in either an anchorage-dependent or an anchorage-independent culture system. In the latter, chondrogenic cells may be cultured as colonies within an agarose gel. Heretofore, only small pieces of cartilage tissue of undefined shape have been prepared using this manner. Furthermore, the resulting cartilage remains embedded within a gel matrix making it less suitable for implantation into mammals. Alternatively, in another anchorage-independent method, chondrocytes may be cultured as colonies in suspension culture. However the resulting particles containing synthetic cartilage-like material are usually small and of undefined shape, and do not integrate with each other and with the surrounding cartilage within the defect. This makes them unsuitable for implantation and repair of a predetermined articular cartilage defect.

In the anchorage-dependent method, primary cultures of chondrogenic cells isolated from primary tissue are grown as monolayer attached to the surface of a cell culture flask (e.g. U.S. Pat. No. 4,356,261). The primary cells derived directly from explant tissue remain capable of producing and secreting extracellular components characteristic of natural cartilage, specifically type II collagen and sulphated proteoglycans. However, it is well known that during in vitro expansion as monolayers, chondrocytes dedifferentiate and lose their ability to form hyaline cartilage in vivo. Until now it has not been possible to prepare large patches of articular cartilage from small pieces of biopsy tissue using the anchorage-dependent procedures of U.S. Pat. No. 4,356,261.

In order to solve the above problems, U.S. Pat. No. 5,723,331 provides a method for preparing in vitro large quantities of synthetic cartilage from small samples of biopsy tissue which, based on the discovery that chondrogenic cells may be isolated from a variety of tissues, e.g. pre-existing cartilage, perichondrial tissue or bone marrow, and expanded in vitro prior to cartilage formation, includes first seeding denuded (i.e. isolated from an enzymatically or mechanically disaggregated tissue) chondrogenic cells, proliferated ex vivo, into a pre-shaped well having a cell contacting, cell adhesive surface, and then culturing the proliferated chondrogenic cells in the well for a time sufficient to permit the cells to secrete an extracellular matrix thereby to form a three-dimensional, multi cell-layered patch of synthetic cartilage. This approach does not yield an optimal integration between the implant and the surrounding cartilage. This far there is no evidence on the phenotypic stability of cells in such preparations.

The use of mesenchymal cells has also been proposed for cartilage repair. Mesenchymal cells are a potential alternative source of cartilage-producing cells. They are generally recognised as pluripotent cells capable of dividing many times to produce progeny cells that can eventually give rise to many tissues, including skeletal tissues such as cartilage, bone, tendon, ligament, marrow stroma and connective tissue. By definition, they can undergo many more divisions. Chondro/osteoprogenitor cells, which are bipotent with the ability to differentiate into cartilage or bone, were isolated from bone marrow (e.g. in U.S. Pat. No. 5,226,914), and subsequently from muscle, heart and granulation tissue. Pluripotency is demonstrated using different culture conditions and adding more or less specific inducers, which elicit differentiation of the stem cells into chondrocytes (cartilage), osteoblasts (bone), myotubes (muscle), adipocytes (fat).

It would be highly desirable to have progenitor cells which are easily obtained such as by muscle biopsy, cultured to yield large numbers, and can be used as a source of chondrocytes or osteoblasts or myocytes. However, the same pluripotency that makes them attractive, conveys the risk of metaplastic differentiation. In other words there is the risk that they could differentiate in an undesired direction (e.g. bone or fat within a cartilage defect). In U.S. Pat. Nos. 5,226,914 and 5,197,985 the cells were absorbed into porous ceramic blocks and implanted, yielded primarily bone. However, U.S. Pat. No. 5,906,934 discloses that under very specific conditions mesenchymal stem cells in a suitable polymeric carrier (such as polyglycolic acid mesh) implanted into a cartilage and/or bone defect will differentiate to form cartilage and/or bone, as appropriate. Also U.S. Pat. No. 5,919,702 discloses chondrocyte progenitor cells isolated from umbilical cord sources, e.g. from Wharton's jelly, and cultured so as to give rise to chondrocytes that can produce cartilage tissue. Also in another attempt to avoid the drawbacks of current cartilage and bone repair techniques which cause bleeding and involve the use of mechanically weak non self-derived material, U.S. Pat. No. 5,866,415 suggests treating cartilage or bone defects with a biological material obtained by attaching in vitro cartilage or bone forming cells to a periosteum of sufficient size to accommodate the defect.

WO/96/41523 and WO96/41620 describe the use of FGFR3 as a marker for mesenchymal skeletal progenitor cells. Such cells do not show a stable phenotype. To initiate differentiation of these cells factors may be added to the cells or in situ, for example an FGF9 antagonist. As indicated above the use of progenitor cells for implantation in the body is counter-indicated due to the danger of metaplastic differentiation.

Transforming growth factor-beta ("TGF-β") refers to a family of related dimeric proteins which regulate the growth and differentiation of many cell types. Members of this family include TGF-β 1, TGF-β 2, TGF-β 3, TGF-β 4, TGF-β 5, morphogenic proteins ("MP") such as MP-121 and MP-52, inhibins/activins (such as disclosed in EP-A-222,491), osteogenic proteins ("OP"), bone morphogenetic proteins (hereinafter denoted "BMP"), growth/differentiation factors ("GDF") such as GDF-1, GDF-3, GDF-9 and Nodal. TGF-β was first characterised for its effects on cell proliferation. It both stimulated the anchorage-independent growth of rat kidney fibroblasts and inhibited the growth of monkey kidney cells. TGF-β family members have been shown to have many diverse biological effects, e.g. they regulate bone formation, induce rat muscle cells to produce cartilage-specific macromolecules, inhibit the growth of early haematopoietic progenitor cells, T cells, B cells, mouse keratinocytes, and several human cancer cell lines. TGF-β family members increase the synthesis and secretion of collagen and fibronectin, accelerate healing of incisional wounds, suppress casein synthesis in mouse mammary explants, inhibit DNA synthesis in rat liver epithelial cells, stimulate the production of bFGF binding proteoglycans, modulate phosphorylation of the epidermal growth factor ("EGF") receptor and proliferation of epidermoid carcinoma cells and can lead to apoptosis in uterine epithelial cells, cultured hepatocytes and regressing liver. TGF-βs can mediate cardio-protection against reperfusion injury by inhibiting neutrophil adherence to endothelium and protect against experimental autoimmune diseases in mice. On the whole, proteins of the TGF-β family are multifunctional, active growth factors and also have related biological activities such as chemotactic attraction of cells, promotion of cell differentiation and tissue-inducing capabilities. Differences in their structure and in their affinity for receptors lead to considerable variations in their exact biological function.

In contrast to the foregoing reports of the ability of TGF-β to induce the production of cartilage-specific macromolecules in muscle cells and chondrocytes, TGF-β was found to act synergistically with fibroblast growth factor to inhibit the synthesis of collagen type II by chicken sternal chondrocytes and in rat chondrocytes. In fact, TGF-β has emerged as the prototypical inhibitor of the proliferation of most normal cell types in vitro as well as in vivo, exhibiting a remarkable diversity of biological activity. TGF-β 1 has been purified from human and porcine blood platelets and recombinant TGF-β 1 is currently available.

Among the sub-family of BMPs, the structures of BMP-1 through BMP-15 have previously been elucidated. The unique inductive activities of these proteins, along with their presence in bone, suggests that they are important regulators of bone repair processes and may be involved in the normal maintenance of bone tissue. Recently, the BMP-12-related subfamily of proteins, including BMP-13 and MP52 (see e.g. WO93/16099 and U.S. Pat. No. 5,658,882), was shown to be useful in compositions for the induction of tendon/ligament-like tissue formation and repair. U.S. Pat. No. 5,902,785 discloses that BMP-12 related proteins are particularly effective for the induction of cartilaginous tissue and that BMP-9 is useful for increasing proteoglycan matrix synthesis and therefore for the maintenance of cartilaginous-tissue. It also describes compositions comprising a BMP-12 related protein and additionally including one or more TGF-β superfamily member proven to be osteogenic, preferably BMP-2, -4, -5, -6 and/or BMP-7 as useful for the regeneration of multiple tissue types (for example at the interface or junction between tissues) and especially useful for the treatment of articular cartilage, in which the articular surface, cartilage, subchondral bone and/or tidemark interface between cartilage and bone need to be repaired. The same patent further describes compositions comprising a BMP-12 related protein together with a protein useful for the maintenance of chondrocytes or cartilaginous tissue such as BMP-9, the said compositions being especially useful for the induction and maintenance of cartilaginous tissue at a site in need of cartilage repair such as an articular cartilage defect.

WO96/14335 discloses, using mRNA prepared from newborn articular cartilage, the isolation of two members of the BMP family, designated Cartilage-derived morphogenetic proteins-1 and -2 (CDMP-1, CDMP-2). Storm et al. (1994) in Nature 368, 639-43 and Chang et al. (1994) in J. Biol. Chem. 269, 28227-34 independently established that CDMP-1 mapped close to the brachypodism locus on chromosome 2 in mice and might be involved in the brachypodism phenotype. Also the expression patterns of CDMP's suggests an important role for these genes in joint morphogenesis. WO98/59035 also discloses a method of maintaining a cartilaginous phenotype in chondrocytes in vitro, comprising culturing the chondrocytes in serum-free medium containing a CDMP and/or BMP.

The table below summarising the TGFβ superfamily members follows (Reddi A H, Nature Biotechnol. 1998, 16:247-52).

The BMP Family in Mammals

| BMP subfamily | Generic name | BMP designation |
|---|---|---|
| BMP 2/4 | BMP-2A | BMP-2 |
| | BMP-2B | BMP-4 |
| BMP 3 | Osteogenin | BMP-3 |
| | Growth/differentiation factor 10 | BMP-3B |
| Op-1/BMP-7 | BMP-5 | BMP-5 |
| | Vegetal related-1 (Vgr-1) | BMP-6 |
| | Osteogenic Protein-1 (Op-1) | BMP-7 |
| | Osteogenic Protein-2 (Op-2) | BMP-8 |
| | Osteogenic Protein-3 (Op-3) | BMP-8B |
| | Growth/differentiation factor 2 (GDF-2) | BMP-9 |
| | BMP-10 | BMP-10 |
| | Growth/differentiation factor 11 (GDF-11) | BMP-11 |
| GDF-5, 6, 7 | Growth/differentiation factor 7 (GDF-7) or cartilage-derived morphogenic protein-3 (CDMP-3) | BMP-12 |
| | Growth/differentiation factor 6 (GDF-6) or cartilage-derived morphogenic protein-2 (CDMP-2) | BMP-13 |
| | Growth/differentiation factor 5 (GDF-5) or cartilage-derived morphogenic protein-1 (CDMP-1) | BMP-14 |
| | BMP-15 | BMP-15 |

Other families of growth factors have been shown to play a role in cartilage formation/differentiation. Among them the fibroblast growth factors (FGFs) are a family of polypeptide growth factors involved in a variety of activities. One of their receptors, FGF receptor 3 (FGFR-3) (Keegan K. et al., 1991 Proc. Nat. Acad. Sci. 88: 1095-99), is known to play a crucial role in chondrogenesis. Point mutations in the fgfr3 gene resulting in a ligand-independent constitutively active protein (which means that the FGF signalling is always active also in the absence of the ligand) cause skeletal abnormalities as achondroplasia and thanatophoric dysplasia.

As already outlined above, although autologous chondrocyte transplantation ("ACT") is becoming a widely accepted technique for repair of joint surface defects ("JSD") it still presents some drawbacks. More in details, this procedure implies in vitro expansion—in the presence of autologous serum—of autologous chondrocytes obtained from an uninvolved area of the joint surface, followed by the implantation of the chondrocyte suspension under a periosteal flap sutured to seal the joint surface defect. Cell expansion is necessary to obtain from a small cartilage biopsy a number of cells sufficient to repair the cartilage defect. Expansion in monolayer result in the loss of phenotypic traits in chondrocytes (Benya and Shaffer. 1982, Cell 30:215-24). To date, however, it is not known how far it is possible to expand chondrocytes without hampering their phenotypic stability and therefore their capacity to form stable hyaline cartilage in vivo, resistant to vascular invasion and endochondral bone formation. Other factors that can affect the capacity of chondrocytes to form cartilage in vivo are the culture conditions, and several factors dependent on the donor such as age and pre-existing joint or systemic diseases. At the end of cell expansion the chondrocyte population is composed of some cells that retain their phenotypic stability, and others that still can proliferate but will not anymore contribute to cartilage repair. To obtain a consistent cell suspension for ACT, it is desirable to determine which is the actual capacity of the cells to form cartilage in vivo and, if necessary, to select stable chondrocytes within the expanded cell population. The importance of this issue is underscored by the large variability in the quality of the repair tissue obtained in a large series (Peterson et al. Clin Orthop [374], 212-234. 2000.) consisting of a range going from hyaline-like cartilage to fibrocartilage to no signs of repair.

Chondrocytes are the only normal skeletal cells known to grow anchorage-independent in agarose cultures (Benya and Shaffer. 1982, *Cell* 30:215-224). This culture system allows a recovery of some of the phenotypic traits that are lost with expansion in monolayer (Benya and Shaffer. 1982, *Cell* 30:215-224). The expression of type 2 collagen and the capacity to grow and rescue phenotypic traits in agarose culture, are good assays to evaluate chondrocyte differentiation and the potential to differentiate respectively. However they do not measure the capacity of chondrocytes to form cartilage in vivo.

SUMMARY OF THE INVENTION

The issues explained above clearly show that there is a long felt need for an assay to measure the capacity of expanded chondrocytes to form stable cartilage in vivo after in vitro expansion independently on the culture conditions and donor-related factors. Among skeletal cells the anchorage independent growth is peculiar of chondrocytes and chondrocytic precursors. Therefore this property is required only when chondrocyte-like cells are of interest. There is also a need to identify molecular markers associated with specific cell types that would allow the clinician to produce suitable implants and to regenerate and repair cartilage tissue with the appropriate cells and avoid scar formation to the greatest possible extent. These goals and other purposes are achieved by means of the following objects of the present invention.

A first object of the present invention is to provide an in vivo assay to measure anchorage independent growth and phenotypic stability of a certain cell population, and more specifically to measure at the same time the anchorage-independent growth of cells and their potential to retain their commitment to a certain (original or induced by manipulation) differentiation pathway. A second object of the invention is the use of the aforesaid in vivo assay to evaluate the risk that a certain procedure or treatment administered to a certain cell population can hamper its anchorage-independent growth as well as its phenotypic stability. A third object of the invention is the use of the aforesaid in vivo assay to predict the outcome of autologous chondrocyte transplantation ("ACT") using a certain population of expanded chondrocytes. A fourth object of the invention is the use of the aforesaid in vivo assay to identify molecular markers linked to the phenotypic stability of a certain cell population. A fifth object of the invention is the definition of a set of molecular markers linked to the outcome of the aforesaid in vivo assay using freshly isolated chondrocytes and therefore to the capacity to form stable cartilage in vivo. A sixth object of the invention is the use of these positive and negative markers of chondrocyte stability as a tool to monitor, passage by passage, in vitro cell expansion and, more in general, the manufacturing process of chondrocyte expansion. This tool will be useful to optimize next generation chondrocyte expansion technologies and to predict when cell expansion must be stopped, to recover chondrocytes that have already lost their phenotypic stability only when needed, and especially to provide a quality control for chondrocytes to be used for ACT for lot release approval. This will make chondrocyte suspensions for ACT a more reliable and consistent product. A seventh object of this invention is the use of FACS (Fluorescence Activated Cell Sorting) analysis and cell sorting in general using positive and negative markers to select, from a chondrocyte population, only those cells that retain their phenotypic stability. Another object is to provide an implant comprising cells selected from a cell population as mentioned above. Another object of this invention is the use of cells selected from a cell population as mentioned above for a variety of clinical applications including transplantation into a patient through surgery or arthroscopic injection, namely to promote the repair or regeneration of damaged joints or joint surfaces, or seeding prosthetic devices. Yet another object of this invention is a therapeutic composition including cells selected by the above method for use in the said clinical applications.

Yet another object of the present invention is to provide a cell culture exhibiting chondrocyte phenotypic stability in which the ratio of cells showing positive and negative markers is controlled.

DETAILED DESCRIPTION OF THE INVENTION

Figure 1:
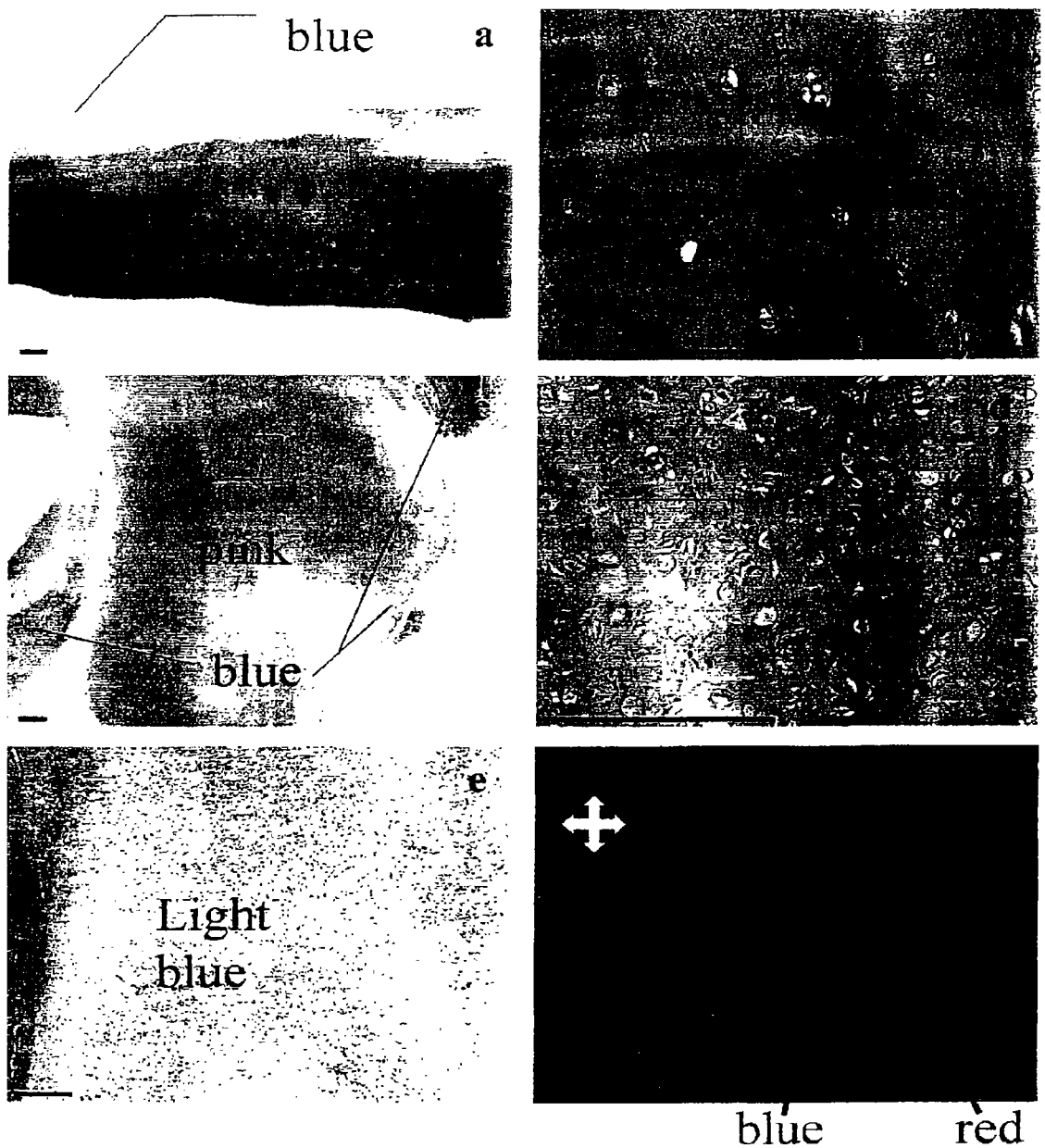
FIG. 1 is a set of 6 pictures showing the histological and histochemical characteristics and the expression of collagen type 2 of implants from the in vivo assay of the invention compared to human adult articular cartilage.

Terms used throughout this disclosure are defined as follows:

Chondrocyte Stability

The capacity of a cell suspension (either obtained from cartilage tissue or from any other tissue containing cells with chondrogenic potential) to produce upon injection in a mammal (in vivo), such as immune-deficient mice, (in a time frame of 3 weeks) a cartilage implant without signs of vascular invasion or endochondral bone formation.

Chondrogenic

The capacity to promote or stimulate cartilage growth, as applied to cells such as chondrocytes and to cells which themselves differentiate into chondrocytes. The term also applies to certain growth factors, such as TGF-β, which promote cartilage differentiation.

Co-Expression and Co-Detectability

With co-expression, in the context of the present invention, is meant that a second factor or marker is expressed or detectable whenever a first factor or marker is expressed oe detectable. For example, whenever BMP-2 or FGFR-3 (positive markers) or ALK-1 or collagen type X (negative markers) are expressed and detectable. As such, the marker is co-detectable with the aforementioned positive and negative markers. Such co-expressed or co-detectable factor or marker can be a recognizable cell surface marker, detectable via polyclonal or monoclonal antibodies and/or specific ligands.

Connective Tissue

As used herein, any of a number of structural tissues in the body of a mammal including bone, cartilage, ligament, tendon, meniscus, dermis, hyperdermis, muscle, fatty, tissue, joint capsule.

Differentiation

A biological process by which primitive unspecialized cells acquire specialised function(s). Terminal differentiation provides a highly specialised cell having unique functional, genetic and phenotypic characteristics.

Marker Protein

A polypeptide that distinguishes one cell (or set of cells) from another cell (or set of cells) in a population of cells and is associated to a peculiar biological function. For example, the surface antigen CD3 is expressed or is detectable on the surface of T lymphocytes but not on other types of lymphocytes (e.g. B, or null lymphocytes) and serves as a marker protein for this subset of lymphocytes. When the marker protein is a cell-surface antigen, like for instance hormone receptor, antibodies that bind the marker protein can be used in cell sorting methods, e.g., to produce a population of cells enriched for cells that express the marker protein. Alternatively, intracellular proteins can be used as marker proteins. For example, fluorescent or luminescent proteins, such as green fluorescent protein (GFP) and aequorin (GFP of *Aequoria victoria*) (Tanahashi et al (1990), *Gene* 96: 249-255) can be used as the marker protein and can facilitate cell sorting, e.g., by FACS. Also enzymes can be used, provided that the activity of the enzyme can be detected. For example, β-galactosidase is well suited for use as a marker protein; this enzyme can be detected by introducing into the cell a substrate(s) that release a fluorescent product(s) upon cleavage by the enzyme (available from, e.g., Molecular Probes). Another suitable enzyme is catechol 2,3-dioxygenase, which is encoded by xy/E of *Pseudomonas putida* (Domen et al (1986), *Anal Biochem* 155: 379-384).

Operably Linked

Connection of a coding sequence and (a) regulatory sequence(s) (e.g., a promoter) in such a way as to permit gene expression when the appropriate molecules (e.g., transcriptional activator proteins) are bound to the regulatory sequence(s).

Osteogenic

The capacity to promote or to generate the production of bone. The term may be applied to osteoblasts which have the capacity to promote bone growth, or to cells which themselves are able to differentiate into osteoblasts. The term would also apply to growth factors having the ability to promote bone growth.

Phenotypic Stability

Maintenance of the ability of any cell to organize or reorganize, in vivo, the structure of a specific tissue, either the original tissue where the cells were taken from, or a different tissue the cells have been forced to form under specific conditions.

Promoter

A nucleotide sequence sufficient to direct transcription of a coding sequence. Included within the invention are those promoters which are inducible by external signals or agents; such elements can be located in the 5' or 3' untranslated regions (UTR) of the native gene. A "FGFR-3 promoter" is any sequence contained within the UTR of the endogenous FGFR-3 gene that is sufficient to direct transcription of FGFR-3 in FGFR-3 positive cells like stable chondrocytes. For example, a 3 kb sequence immediately adjacent to the FGFR-3 transcription start site is sufficient to direct FGFR-3 gene expression. It is recognized that in genetic constructs containing a FGFR-3 promoter (e.g., those constructs that also contain a reporter gene or a gene encoding a marker protein), minor variations (e.g., deletions, point mutations, and the like) can be made in the sequence of the FGFR-3 promoter without abrogating its ability to be active in phenotypically stable chondrocytes and not in other chondrocytes. Thus, FGFR-3 promoters having such minor variations without abrogating the specificity of the promoter are encompassed by the term "FGFR-3 promoter". In addition, multiple copies of the FGFR-3 promoter, arranged in tandem, can be used to direct gene expression.

Reporter Gene

Any gene for which expression can be monitored. Commonly used reporter genes include, for example, genes encoding chloramphenicol acetyltransferase, alkaline phosphatase, luciferase, and green fluorescent protein.

Stable Cartilage

Cartilage not finally turning into bone, i.e. cartilage devoid of any signs of vascularization. Particularly, the stable cartilage in accordance with the present invention is human adult or mature articular cartilage but may also include animal adult or mature cartilage. Contrary to stable cartilage, transient cartilage in the end will become bone tissue. In the context of the present invention, cartilage is said to be stable if, even after e.g. seven weeks, any signs of bone formation are absent.

Stem Cell

Pluripotent precursor cell having the ability to self-renew and to generate a variety of differentiated cell types. True stem cells can divide indefinitely. With embryogenic stem cells are understood the pluripotent cells of normal karyotype derived from a blastocyst.

DETAILED DESCRIPTION OF THE EMBODIMENTS AND EXAMPLES

The present invention is based on the possibility to measure and verifiably ascertain the capacity of isolated chondrocytes to produce cartilage in vivo using a nude mouse model. First, this capacity is linked to a set of molecular markers. Secondly, the presence of the molecular markers is associated with the outcome of joint surface defects ("JSD") repair in well-standardised animal models of JSD. Thirdly, membrane-associated molecular markers can be used to select, from an expanded chondrocyte population, only those cells that, retaining their phenotypic stability, will be able to optimally repair JSD. The set of molecular markers (both membrane-associated and/or non membrane-associated) can also be used as a final quality control for the cell suspension to be used for ACT or the repair of the cartilaginous structures, thus providing a reliable and consistent final product.

A first embodiment of the present invention consists of an in vivo assay which measures the capacity of isolated cells to reproduce in vivo a certain tissue with all Its cellular and extra-cellular components, i.e. all its specific characteristics. This assay—devised to measure chondrocyte stability but extendable to any cell population involved in a certain differentiation pathway—consists of an in vivo assay to measure anchorage-independent growth and phenotypic stability of a certain cell population comprising subcutaneous or intramuscular injection in a mammal of a cell suspension of articular chondrocytes in an iso-osmotic liquid, the same suspension comprising articular chondrocytes in an amount equivalent to at least $1\times10^6$ (preferably from $2\times10^6$ to $20\times10^6$) chondrocytes as applied to immune-deficient mice. In the case that the mammal is a mouse, the in vivo assay consists of the injection of a single cell suspension intramuscularly in immune-deficient nude mice. After a certain period of time, at least 3 weeks, the mouse is sacrificed, dissected, and the implant, if retrieved, weighed, fixed and histologically evaluated. The in vivo assay of the invention is highly specific since about $5\times10^6$ freshly isolated articular chondrocytes injected in a volume of 50-100 µl of any iso-osmotic liquid such as phosphate buffered saline (PBS) or HBSS, are sufficient to yield after 3 weeks an implant of mature cartilage. The same number of expanded periosteal cells yield a fibrous tissue histologically resembling periosteal tissue. Young periosteal derived cells (PDCs), i.e. PDCs from individuals younger than 20 and preferably younger than 16, cultured and expanded under appropriate conditions, however, yielded stable cartilage implants. On the contrary, the injection of cell lines known to have in vitro osteo-chondrogenic potential—namely ATDC5, CFK2, RCJ, and C5.18 cells—did not yield any retrievable implant. Importantly, serially passaged (P4 and P5) articular chondrocytes, still retaining their anchorage-independent growth and rescuing the expression of type 2 collagen in agarose culture (according to the method of Benya et al. (1982) Cell (1):215-24) failed to yield any implant. This finding is of particular importance because demonstrates that the agarose assay—thus far considered a stringent assay for the phenotypic stability of expanded chondrocytes (Brittberg et al. N Engl J Med. 1994 Oct. 6; 331(14): 889-95)—is not sufficient to predict the capacity to form cartilage in vivo. From this the well-known agaraose assay is unable to function as a quality control method for determining when cartilage is in a suitable state to be implanted. Strikingly epiphyseal chondrocytes (which in normal embryonic development undergo endochondral ossification and are destined to be substituted by bone) yield a cartilaginous implant in which vascular invasion, chondrocyte hypertrophy and bone formation are taking place.

A second embodiment of the invention is the use of certain specific conditions of the in vivo assay of the first embodiment to evaluate the possibility that a certain procedure or treatment administered to a certain cell population involved in a certain differentiation pathway can hamper its anchorage-independent growth as well as its phenotypic stability. For instance, while enzymatic release of the cells by enzymatic treatment induces no such risk, on the contrary extensive cell expansion (after 2-3 passages) compromises the ability of chondrocytes to yield a cartilaginous implant in the in vivo assay. On the other hand, the in vivo assay also evaluates whether a certain treatment, such as addition of growth factors/reagents, or procedure, such as physical stimulation, enhances the phenotypic stability of cell populations. For instance, treating the cell suspension for 30 minutes with CDMP-1 (100 ng/ml; stock solution in 45% acetonitrile, 0.1% trifluoroacetic acid) just before injection, followed by washing two times in PBS, resulted in a three fold increase in the wet weight of the retrieved implant as compared to control injections, and in a 2 fold increase in the number of cells. Such enhancement can allow a dramatic reduction of the expansion needed for JSD repair (in some cases and ultimately making in vitro expansion not needed at all) and consequently a corresponding reduction of the risk to make chondrocytes phenotypically unstable.

A third embodiment of the invention is the use of the in vivo assay of the first embodiment to predict the outcome of autologous cell transplantation ("ACT") using a certain population of cells involved in a certain differentiation pathway (e.g. expanded chondrocytes) as a means to predict phenotypic stability (e.g. chondrocyte stability). This can be evaluated either using well-standardised animal models for ACT or using an ex vivo system. This ex vivo system consists of placing articular cartilage, with or without underlying bone, in culture (liquid, solid or semi-solid), producing a cartilage defect, with or without a natural or synthetic membrane to cover the lesion, and applying, underneath the membrane, a cell population either in suspension, or seeded within a carrier, with or without growth factors to mimic in vitro the events that take place in vivo during JSD repair.

A fourth embodiment of the invention is the use of the in vivo assay of the first embodiment to identify molecular markers linked to the phenotypic stability of a certain cell population involved in a certain differentiation pathway, e.g. chondrocytes. These molecular markers can be identified by semi-quantitative RT-PCR, by Northern hybridisation (as explained in example 4 below), by the generation of subtracted libraries from cell population that succeed in the in vivo assay matched to similar cell populations that fail (e.g. serially passaged chondrocytes), by differential display or subtractive hybridisation approaches, or by DNA arrays or DNA chips. Such DNA chips can hold all known genes involved and/or just not involved with chondrocyte stability. EST (expressed sequence tags) can be used to identify and provide information on previously unknown genes. A set of such genes can be identified by comparing the outcome of cell populations that form good cartilage and preferably stable cartilage with the outcome of cell populations that fail to do so. A third population used in the comparative test may comprise a chondrocyte population that forms cartilage in vitro as long as a trigger is present (e.g., TGF-β1), but that loses this capacity once the trigger is removed from the culture medium and that fails to form a retrievable cartilage implant in vivo. A set of positive and negative markers for chondrocyte phenotypic stability, consisting of at least 2 and preferably at least 20 markers is needed to monitor efficiently and unequivocally chondrocyte quality. Preferably, the outcome is linked to ratios of markers or thresholds therefor (taking into account differences in expression and possible gradual upregulation or downregulation of markers). Preferably the predictive value of the set of markers is further increased by analyzing the effect of independent variables (age, gender, background, co-morbidities) on the final outcome of the ACT procedure. This can be done storing in a database all the data of the individual patient together with the expression of the molecular markers and a score that describes the outcome of the procedure (based on pain, function of the joint, stiffness of the repair tissue by indentometry, and eventually histologic and molecular analysis of biopsy of the repair tissue). The influence of the independent variables on the predictive value of our set of markers will be determined by statistical analysis of the data.

DNA chips (or genosensors) are miniature arrays of surface-tethered (c) DNA probes (typically oligonucleotides but also longer DNA probes) to which a nucleic acid sample (the "target" sequence) is hybridized. In the context of the present invention, DNA chips can be used as diagnostic tools to rapidly conclude on chondrocyte phenotypic stability. The aim is to produce digital hybridization fingerprints that can be interpreted by computer and for which ratios of "positive" and "negative" markers can be generated. Genosensors can harbour hundreds to thousands (e.g., 12,000) of DNA probes, useful for high throughput DNA marker analysis and messenger RNA profiling (differential display on a chip). Alternatively, smaller sets of probes, duplicated in subarrays across the chip, can be used to interrogate numerous samples in parallel. Oligonucleotides are either synthesized in situ on the support surface of the DNA chip (in situ attachment strategy), or, alternatively, presynthesized oligonucleotides are attached to each site in the array (post-synthesis attachment strategy). The phosphoramidite method of solid phase chemical synthesis is used to generate the oligonucleotides in both cases (Matteuci and Caruthers (1981), *J Am Chem Soc* 103: 3185-91). The post-synthesis attachment strategy is, easy to implement using commercially available equipment and materials (Beattie, In Caetano-Anolles, Gresshoff (ed), *DNA Markers. Protocols, applications and overviews*. Wiley-VCH, New York, p 213-224). More advanced options are available for preparation of higher density arrays (Microfab technologies Inc.: Eggers et al, (1994), *BioTechniques* 17: 516-525; Accelerator Technology Corp.: McIntyre (1996), *IBC Conference on Biochip Array Technologies*, Marina del Rey, Calif.; Mirzabekov group: Yershov et al (1996), *Proc Natl Acad Sci USA* 93: 4913-4918; Khrapko et al (1991), *FEBS lett* 256: 118-122; Mirzabekov (1994), *Trends Biotechnol* 12: 27-32). Support surfaces comprise glass, such as microscopy slides, and microchannel glass (Tonucci et al (1992), *Science* 258: 783-785) or porous silicon (Lehmann (1993), *J Electrochem Soc* 140: 2836-2843) for use in a flowthrough genosensor (Beatti et al, (1995), *Clin Chem* 41: 700-706). In the latter, hybridization occurs within three-dimensional volumes, providing an approximately 100-fold greater surface area per unit cross section compared with two-dimensional flat surface designs, greatly increasing thereby the binding capacity per hybridization cell and providing an improved detection sensitivity etc. (Doktycz and Beattie (1996), in: Beugelsdiik A (ed), *Automated Technologies for Genome Characterization*. John Wiley & Sons, New York; Beattie (1996), In: Sayler G S (ed), *Biotechnology in the Sustainable Environment*. Plenum Publishing Corp, New York; Beattie et al (1996), In: Schlegel J (ed), *Pharmacogenetics: Bridging the Gap between Basic Science and Clinical Application*. IBC Biomedical Library, Southborough, Mass. Oligonucleotide probes are covalently linked to, e.g., silicon dioxide surfaces by applying the methods of Lamture et al (1994), *Nucleic Acid Res* 22: 2121-2125; Beattie et al (1995), *Clin Chem* 41: 700-706, *Mol Biotechnol* 4: 213-225; Doktycz and Beattie (1996), In: Beugelsdiik A (ed), *Automated Technologies for Genome Characterization*. John Wiley & Sons, New York; Beattie (1996), In: Sayler G S (ed), *Biotechnology in the Sustainable Environment*. Plenum Publishing Corp, New York; or Beattie et al (1996), In: Schlegel J (ed), *Pharmacogenetics: Bridging the Gap between Basic Science and Clinical Application*. IBC Biomedical Library, Southborough, Mass. Protocols for attachment to glass surfaces, using 3'-propanolamine oligonucleotids (Genosys Biotechnologies, The Woodlands, Tex.) and to microscopy slides are available from Beattie (Caetano-Anolles, Gresshoff (ed), *DNA Markers. Protocols, applications and overviews*. Wiley-VCH, New York, p 213-224) and Beattie et al (1995), *Mol Biotechnol* 4: 213-225. A robotic fluid dispensing system is commercially available (e.g. Hamilton Microlab 2200 system equipped with 21 G needles and 50 µl syringes), capable of robotically dispensing droplets as small as 10 nL onto glass slides at 1 mm center-to-center spacing (Beattie et al (1995), *Clin Chem* 41: 700-706, *Mol Biotechnol* 4: 213-225).

Genosensors and diagnostics in accordance with the present invention may be used to diagnose the state of cells and cell cultures but may also be used in situ to determine the vitality of human or animal cartilage.

A fifth embodiment of the invention is the identification of a set of molecular markers linked to the outcome of the in vivo assay of the first embodiment, using freshly isolated or serially passaged cells from a certain cell population involved in a certain differentiation pathway, e.g. chondrocytes, and therefore linked to the phenotype (e.g. chondrocyte) stability. For instance, freshly isolated human chondrocytes were used for RNA purification and cultivated in vitro. Upon passaging, an aliquot of cells was used for RNA purification, 2 aliquots of $5 \times 10^6$ cells were injected in the in vivo assay and the rest re-plated. RNAs were tested by semi-quantitative RT-PCR for expression of genes known to have a role in chondrogenesis and cartilage maintenance.

In the PCR analysis were also included genes isolated from a subtracted cDNA population obtained by a subtractive hybridization approach: cDNA from pig P0 chondrocytes (stable in the in vivo assay) was matched against cDNA from P1 chondrocytes (that failed to yield an implant) in a two-way subtractive hybridisation. Individual cDNAs from both subtracted cDNA populations (P0-P1 and P1-P0) were cloned in PCR-Script Amp SK(+) vector, and sequenced. The human homologs, when known, were included in the RT-PCR analysis. Unknown cDNAs were evaluated for differential expression by Northern analysis.

Results indicate the high expression of BMP-2, FGFR-3, and type II collagen as positively associated to chondrocyte stability, whereas activin-like kinase (ALK)-1 and collagen type X expression are negatively associated. The absence of a negative marker can be interpreted as a positive marker.

Other markers coexpressed with respectively FGFR-3 or BMP-2 and ALK-1 and that therefore predict their expression, can be used for quality control and fall within the scope of the present invention. The molecular marker expression can be detected at the mRNA level (e.g., via RT-PCR), at the protein level (e.g. via specific antibodies—polyclonal or monoclonal—via specific ligands (e.g., FGF9 is a specific ligand of FGFR-3). Fluorochrome-labelled FGF-9 could be used to select FGFR-3 expressing cells via FACS, or FGF-9 coated magnetic beads could be used to sort FGFR-3 expressing cells via a magnetic field (Dynabeads).

Alternatively, the detection of the molecular markers (e.g. FGFR-3) can be indirect via specific target genes or any other component of the FGFR-3 pathway, via reporter constructs (indirect method based on detection of FGFR-3 promoter activity or promoters that are specifically activated upon FGFR-3 signalling controlling the expression of a heterologous reporter gene). Polyclonal or monoclonal antibodies are preferentially raised against the extracellular domain of the receptor so that the antibodies can be used for cell sorting like FACS (see above). More specifically, that is hydrophilic and therefore readily accessible and that is specific to FGFR-3. Mouse, rabbit, or any other suitable species IgM/IgG antibodies of the present invention are raised against a fragment of FGFR-3, e.g. against the region between the I and the II immunoglobulin-like loop of the extracellular domain of the FGFR-3. A peptide suitable for raising suitable antibodies has the amino acid sequence TGLVPSERVLVGPQRLQVL-NASHEDSGAYSCRQRLTQRVL (SEQ ID NO: 1). The full nucleotide sequence of the FGFR-3 receptor is publicly available (Genbank accession number NM_000142) Antibodies raised against other such domains of the FGFR-3 receptor fall within the scope of the present invention. Methods for raising such antibodies are well known in the art and are for instance described In Ausubel et al (ed), *Short Protocols in Molecular Biology*, 4$^{th}$ edition, John Wiley & Sons, New York, and more specifically units 11.3, 11.4 and 11.5; In Paul (ed), *Fundamental immunology*, 4$^{th}$ edition, Lippincott-Raven Publishers, New York, and more specifically chapter 4, p 101 ef; de St. Groth and Scheidegger (1980), *J immunol Methods* 35:1-21; French et al (1986), *Immunol Today* 7:344-346; Langone and Vunakis (1986), *Methods in Enzymology*, vol 121, *Immunochemical Techniques. Part I, Hybridoma technology and monoclonal antibodies*. Orlando: Academic Press; Hämmerling et al (1981), *Monoclonal antibodies and T-cell hybridomas. Perspectives and technical advances*. Amsterdam: Elsevier/North-Holland Biomedical Press; Yokoyama (1995) In Coligan et al (ed), *Current protocols in immunology*, Wiley & Sons, New York, 2.5.1-2.2.17; Kohler and Milstein (1975), *Nature* 256: 495-497. Also possible is the derivation of monoclonal antibodies from e.g. phage display libraries (Paul (ed), *Fundamental immunology*, 4$^{th}$ edition, Lippincott-Raven Publishers, New York, and more specifically chapter 4, p 101 ef; de Bruin et al (1999), *Nature Biotechnology* 17(4): 397-399).

A sixth embodiment of the invention is the use of the positive and/or negative markers of phenotype (e.g. chondrocyte) stability identified in the fifth embodiment, either individually or in combination, as tools to monitor passage by passage cell expansion, namely to predict when cell expansion must be stopped and/or to recover cells (e.g. chondrocytes) that have already lost their phenotypic stability only when needed, and eventually to provide a means for quality control of cells (e.g. chondrocytes) to be used for autologous cell transplantation ("ACT"), thus making cell (e.g. chondrocyte) suspensions for ACT a more reliable and consistent product.

A seventh embodiment of this invention is the use of FACS analysis and other cell sorting methods to select, from a cell (e.g. chondrocyte) population, only those cells that retain their phenotypic stability. "Positive" membrane-associated markers (e.g. FGFR-3 or markers co-detectable with FGFR-3, FGFR-3 reporter activity, or components of the FGFR-3 signalling pathway that report FGFR-3 activation) will be used for positive selection of cells with phenotypic stability (e.g. stable chondrocytes), while "negative" membrane-associated markers (e.g. ALK-1 or markers co-detectable with ALK-1) will be used to sort out cells without phenotypic stability (e.g. unstable chondrocytes). The positive and negative markers may be used individually or combined. The consistency of the selection will be monitored by the detection of unrelated, non membrane-associated markers such as BMP-2 and type II collagen in the sorted population, thus significantly enriching the cell population to be used for ACT with cells with phenotypic stability (e.g. stable chondrocytes) and consequently increasing quality and efficiency of the whole procedure. FACS is one of the conventional cell sorting methods used to sort a specific cell population out of a heterogeneous cell suspension. Antibodies raised against specific cell markers are labelled to fluorochromes and are used to label the cell population that expresses that marker. The fluorescence is used to sort individual cells by mean of a specific technology (Beckton Dickinson). Methods to fluorescently label antibodies are known in the art and many such antibodies are commercially available. Alternatively, an unlabeled antibody can be use to specifically bind the cell surface polypeptide, and a second, labelled antibody can then be used to specifically bind the first antibody. Other techniques, such as the use of protein-conjugated magnetic beads that selectively bind particular cells, can also be used. Suitable kits are commercially available. Generally, such kits utilize a tagged antibody (e.g., a biotin-labelled antibody) to bind the cell surface marker protein. The antibody-bound cells are contacted with a magnetic bead-protein conjugate, where the protein portion of the bead-protein conjugate specifically binds the tagged antibody. For example, a streptavidin-magnetic bead conjugate can be used to bind the biotin-tagged antibody to produce a complex containing the magnetic bead-protein conjugate, the tagged antibody, and the cell expressing the marker protein. Such complexes can be separated from other cells by temporarily adhering the complex to a magnet and separating the adhered cells from the other cells (i.e., a population of cells depleted for, e.g., phenotypically unstable chondrocytes). Magnetic beads that are covalently coupled to a secondary antibody are commercially available. Other antibody-based methods for sorting cells, like the use of affinity chromatography or the retaining of cells expressing the particular cell surface proteins via Petri dishes coated with antibodies directed against the latter, also are known in the art and can be used in the invention. A useful, commercially available affinity cell separation kit, "CEPRATE LC", may be obtained from CellPro (CellPro, Inc. Bothell, Wash. 98021).

Methods of cell sorting may involve selecting cells based on suitable ratios, e.g. the ratio of cells expressing a positive marker mentioned above to a negative marker mentioned above. Preferably, the ratio is such that the cells with positive markers are in the majority, that is the ratio of cells with positive to cells with negative markers is 1 or greater than 1, preferably 2 or greater than 2.

Another embodiment of this invention comprises cells and in using cells retaining phenotypic stability and selected from a cell population by means of the above selection method for a variety of clinical applications. The cells are typically human adult or mature cells exhibiting phenotypic stability. The cells are particularly human adult or mature articular cartilage cells but may also include animal adult or mature cells exhibiting the same properties. These cells, may for instance, be transplanted without further processing to a connective tissue site in a patient to promote the repair or regeneration of damaged bone or cartilage. Unlike previous methods, the present invention does not necessarily require (as explained in the second embodiment) in vitro culturing in order to obtain a suitable (both in nature and quantity) cell population for use for in vivo application. By way of example, the said selected cells retaining phenotypic stability may be implanted at any connective tissue site needing cartilage regeneration by any implanting procedure such as surgery or arthroscopic injection. Another clinical application of such cells involves seeding any prosthetic device intended to be anchored into a mammal host in order to improve the attachment of the said device This includes knee and hip replacement devices made from organic or inorganic materials having low immunogenic activity such as titanium alloys, ceramic hydroxyapatite, stainless steel and cobalt-chrome alloys. Another example is the use of said cell population to create and improve sphincter function by means of the formation and maintenance of a cartilaginous support, for instance around the urethra for stress incontinence.

In yet another embodiment the ratio Cell+/Cell− of cells expressing BMP-2 and/or FGFR-3 and/or markers co-detectable with these markers and/or specific reporter constructs or molecules belonging to the specific intracellular signalling pathways as molecular markers positively associated with chondrocyte phenotypic stability to activin-like kinase-1 (ALK-1) and/or markers co-detectable with this marker and/or specific reporter constructs or molecules belonging to the specific intracellular signalling pathways as molecular markers negatively associated with chondrocyte phenotypic stability is greater than 1, preferably greater than 2. The cells or cell culture may be in a form suitable for implantation in a human or animal.

Yet another embodiment of this invention consists of a therapeutic composition including cells selected by the above method for use in the said clinical applications. The cells are mature or adult cells which exhibit phenotypic stability. In addition to the selected cells, the composition usually includes at least a pharmaceutically acceptable carrier, well known to those skilled in the art and for instance selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregeletanized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like. When the therapeutical composition is intended for transplantation to a site in the body needing repair, it may additionally include at least one growth factor of the TGF-β family.

A more complete understanding of the present invention will be obtained by referring to the following illustrative examples.

Example 1

Cartilage Obtainment and Cell Isolation

Articular cartilage was obtained, within 24 hours after death unless otherwise indicated from human donors not having suffered from any articular disease. After macroscopic inspection to rule out gross joint pathologies, cartilage was sliced full thickness from femoral condyles and placed in Hank's Balanced Salt Solution ("HBSS") (available from Life Technologies) supplemented with 200 units/ml penicillin, 200 µg/ml of streptomycin, and 0.5 µg/ml of amphotericin B (Life Technologies). After two washes in HBSS during 5 minutes at 37° C., cartilage was finely minced and placed in a sterile 0.2% crude collagenase (Life Technologies) solution in Dulbecco's Modified Eagle Medium ("DMEM") with high glucose (Life Technologies) containing 10% foetal bovine serum ("FBS") (Biowittaker), 200 units/ml penicillin, 200 µg/ml of streptomycin, and 0.5 µg/ml of amphotericin B. After overnight incubation at 37° C., cells were washed twice in culture medium—DMEM supplemented with 10% FBS, 100 units/ml penicillin, 100 µg/ml of streptomycin, and 0.25 µg/ml of amphotericin B—and counted with trypan-blue exclusion test to adjust for the number of viable cells.

Example 2

In Vivo Assay

Cells isolated in example 1 were washed twice in sterile phosphate buffered saline ("PBS"), re-suspended in a volume of 100 µl of PBS and injected intramuscularly in the thigh of female, 4-5 weeks old immune-deficient nude mice. Animals were sacrificed after 3 weeks by cervical dislocation and the thigh dissected to retrieve the presence of the implant in the site of injection. Implants were weighed, and either snap-frozen and stored in liquid nitrogen for in situ hybridisation or fixed in freshly-made 4% formaldehyde for 4 hours for histology and immunohistochemistry. After fixation the samples were included in paraffin, cut in 5 µm thick sections and coloured according to standard protocols (Alcian blue pH 2.5, Toluidine blue, Masson's trichrome, Safranin O) (Manual of Histological Techniques). Different amounts of cells, from $20 \times 10^6$ to $5 \times 10^5$ were used for injection in order to establish the minimum amount of cells that yielded a cartilage implant. Although the minimal amount of freshly isolated chondrocytes that yielded an implant was $1 \times 10^6$, as an optimal amount we chose to use $5 \times 10^6$ cells because this number always yielded at least one implant in duplicate injections when freshly isolated chondrocytes where used.

FIG. 1 shows that freshly isolated or early passage adult human articular chondrocytes generate cartilage tissue after intramuscular injection in nude mice. (a) and (b) Safranin O stainings of adult human articular cartilage harvested from the femoral condyle. (c) and (d) Safranin O staining of a cartilage implant. (b) and (d) are details from (a) and (c) as indicated by the boxes in (a) and (b), respectively. Compared to adult human articular cartilage, the implant is hypercellular. Masson's trichrome staining in (e) displays the absence of neoangiogenesis or endochondral bone formation. (f) Immunofluorescence for collagen type 2 is brightly positive in the ECM of the implant. Dark spots are blue. Lighter colour is red. Adjacent muscle tissue is indicated with an asterisk. Nuclei are counterstained with DAPI. The scale bar is 200 µm.

In order to check that viable cells were needed to organise the cartilage implant, an equal number of cells that had been killed by freezing and thawing three times in liquid nitrogen were injected. Those injections yielded no implant. We also investigated whether cells should be able to proliferate, we irradiated freshly isolated chondrocytes with a single dose of 50 Gy, a dose that blocks proliferation but is not lethal to the cells. Except for some cytological atypies, the injections yielded an otherwise normal hyaline cartilage implant.

Strikingly, the injection of embryonic epiphyseal chondrocytes (which in normal embryonic development are replaced by bone) yield implant with vascular invasion and endochondral bone formation. These data demonstrate the fine specificity of the in vivo assay in reporting the phenotypic pathway the injected cell is placed in.

Figure 2:
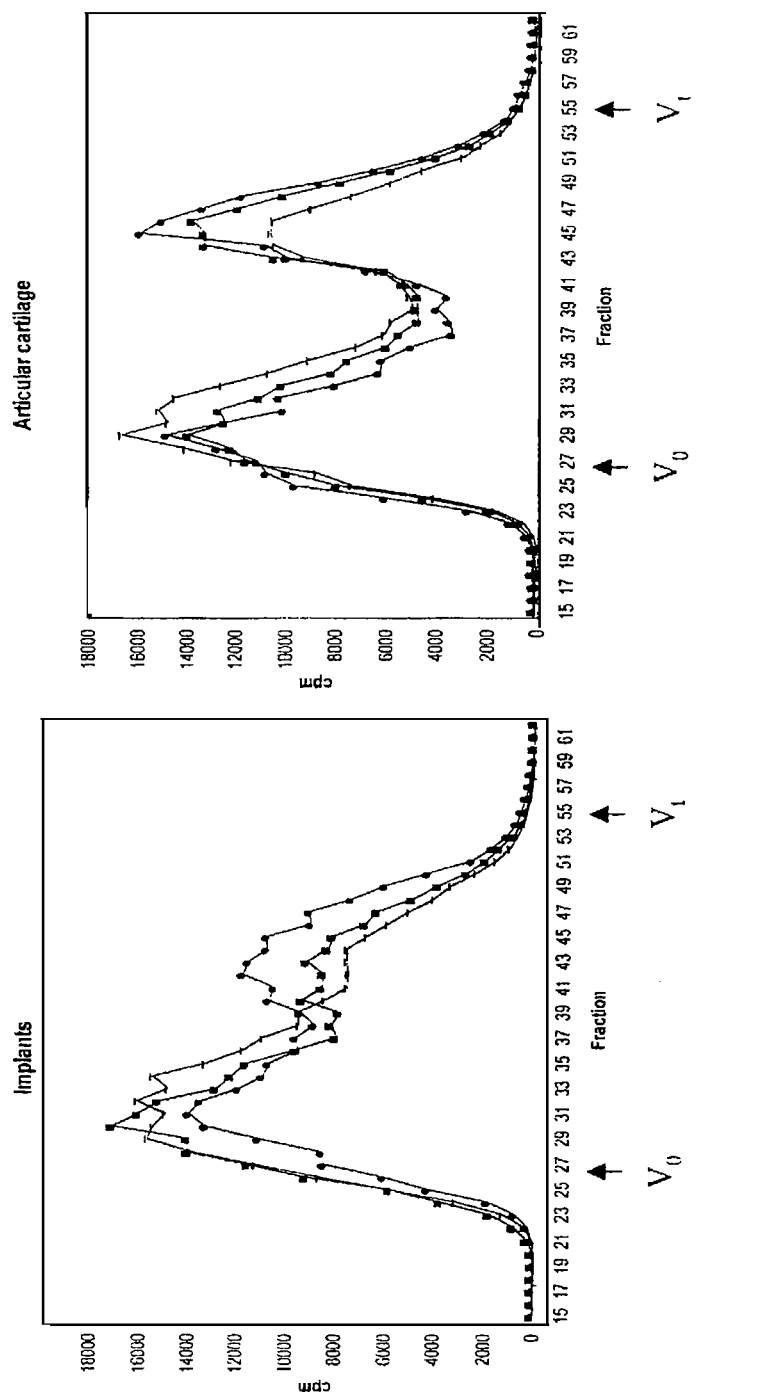
FIG. 2 are two charts (A, B) showing the hydrodynamic profile of sulphated proteoglycans in implants (A) from the in vivo assay of the present invention and in human adult articular cartilage (B).

To investigate the hydrodynamic profile of sulphated proteoglycans (an important component of the extracellular matrix of cartilage) we performed [35S]SO4 incorporation and size fractionation of macromolecules in both the implants and the native human articular cartilage. FIG. 2 shows the presence in 3 implants (A) of high molecular weight proteoglycans with the same hydrodynamic size as in adult human articular cartilage explants (B). The high molecular weight proteoglycans (left peak) are present in both implants and articular cartilage. This molecular weight fraction is specific for cartilage tissue.

Figure 3:
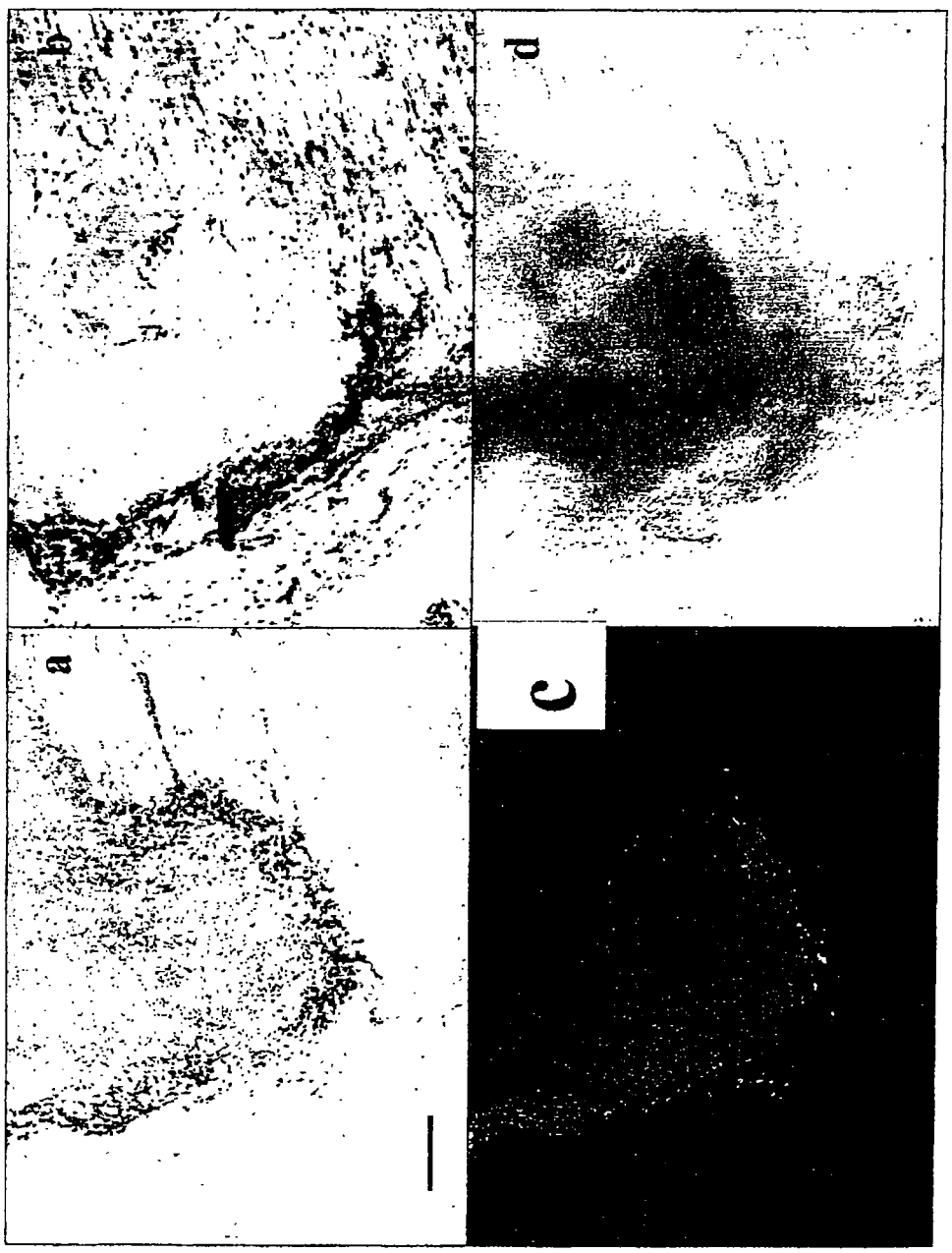
FIG. 3 is a set of four pictures showing in situ hybridisation for human-specific Alu repeats (A), mouse specific L1 repeats (B), a supposition of A and B (C) and toluidine blue staining (D) of an implant from the in vivo assay of the invention.

In order to investigate whether the cartilage implant is made of cells of human origin, i.e. to rule out that the only role of the injected cells is producing factors that induce chondrogenesis in the mouse muscle), we performed in situ hybridisation for human specific Alu repeats as described by Kuznetsov et al. (1997), *J Bone Miner. Res*. (9):1335-47 and mouse-specific L1 repeats. This procedure demonstrated that cells contributing to cartilage formation in our in vivo assay are of human origin, i.e. derive from the injected cells and not from the mouse host. FIG. 3 shows the origin of the implant. Consecutive sections where hybridized with human (a) or mouse (b) specific probes recognizing genomic repeats (Alu and m-L1 respectively). (c) is a superimposition of (a) and (b) using artificial colors. The intermingling of human and mouse cells at the left edge of the implant was due to infiltration of chondrocytes in between the muscle fibers as showed in the toluidine blue staining in (d). The scale bar is 200 µm.

Example 3

Serial Passaging Results in Impaired Chondrocyte Stability

Cartilage samples from 3 independent human donors were placed in monolayer culture. Upon passaging, an aliquot of cells was destined to duplicate injection in the in vivo assay of example 2 and to RNA isolation. Chondrocyte stability, as measured by the retrieval of a cartilage implant after 3 weeks in the site of injection, was lost between passage 1 and 3.

Example 4

Molecular Markers Associated with Chondrocytic Stability

Three pools of human articular chondrocytes were obtained as described in example 1 and cultured in monolayer. Upon passaging, 2 aliquots ($5 \times 10^6$ cells each) were injected in the in vivo assay of example 2, a smaller aliquot was used to obtain the RNA extract and the rest was re-plated. Total RNAs were reverse-transcribed using Thermoscript (available from Life Technologies) and used for semi-quantitative PCR analysis. After passage 5, two samples were placed in low melting-agarose cultures, a system known to result in a rescue of type II collagen expression by de-differentiated chondrocytes. After 2 months, colony formation was abundant and cultures were harvested for RNA extraction. Semi-quantitative RT-PCR analysis was carried out for expression of genes involved in chondrogenesis.

In order to explore the role of genes unknown to be involved in chondrogenesis, we also undertook a differential expression analysis based on the principle of subtractive hybridisation: pig articular chondrocytes were plated and cultured in monolayer. Upon passaging cells were assayed for chondrocyte stability and RNA was isolated. Poly A$^+$ RNA was purified using Oligotex mRNA Mini Kit (available from Quiagen) from total RNA derived from P0 and P1 cells. We chose those two populations because P0 cells still yielded a cartilage implant in the in vivo assay of example 2 while P1 cells did not. cDNAs were reciprocally subtracted in order to obtain species differentially expressed by P0 cells (potential positive markers of stable chondrocytes) and species differentially expressed by P1 cells (negative markers). Subtraction and amplification of subtracted cDNAs were performed using PCR-Select™ cDNA subtraction Kit (available from Clontech). cDNAs were cloned in PCR Script amp SK (+) vector and sequenced. Genes of which human homologue was known were included in the semi-quantitative RT-PCR analysis on human samples, while unknown genes were controlled for their differential expression in the original RNA population by Northern analysis. The detailed procedures used were as follows:

RNA Preparation

Total RNA from chondrocytes was isolated using Trizol reagent (available from Life Technologies), ethanol precipitated and stored at −70° C. for further use. Total RNA from agarose cultures was obtained by homogenising the whole culture in 6M urea, 3M lithium chloride with a Polytron homogeniser, and the major part of agarose was removed by centrifugation at room temperature at 3000 rpm for 15 minutes. Nucleic acids in the supernatant were allowed to precipitate overnight at 4° C., pelletted by centrifugation 15 minutes at 18000 rpm at 4° C., supernatant was removed, RNA was air dried and dissolved in RNAse-free water. Residues of agarose and other contaminants were removed by phenol-chlorophorm extraction followed by ethanol precipitation. Samples were re-dissolved in RNAse-free water and stored at −70° C. for further use. For those samples requiring mRNA selection, poly A$^+$ tailed RNA was sorted out of total RNA by double selection using Oligotex mRNA Mini Kit (Quiagen).

Semi-Quantitative RT-PCR Analysis

1 µg of total RNA was first strand-transcribed using Thermoscript (Life technologies). Before PCR analysis, cDNAs were equalised for β actin. PCR for human β actin was carried out in a volume of 10 µl stopping the reaction after 18, 19, 20 cycles to make sure that PCR amplification was still in an exponential phase. PCR products were electrophoresed in 1% agarose gel in TBE buffer, stained with ethidium bromide and the intensity of the bands was analysed by densitometry using Image Master software (available from Pharmacia-Biotech). cDNAs were diluted according to the relative intensity of the bands. To rule out that β actin was differentially regulated in the different samples to be compared, the same analysis was also performed for GAPDH mRNA. After equalisation for β actin, all samples were simultaneously tested for a number of genes known to be involved in chondrogenesis and cartilage maintenance. The same analysis was performed for those molecules obtained with a subtractive hybridisation approach. For each gene, cycling was optimised in such a way that amplification was still in an exponential phase when PCR was stopped for all samples.

Figure 4:
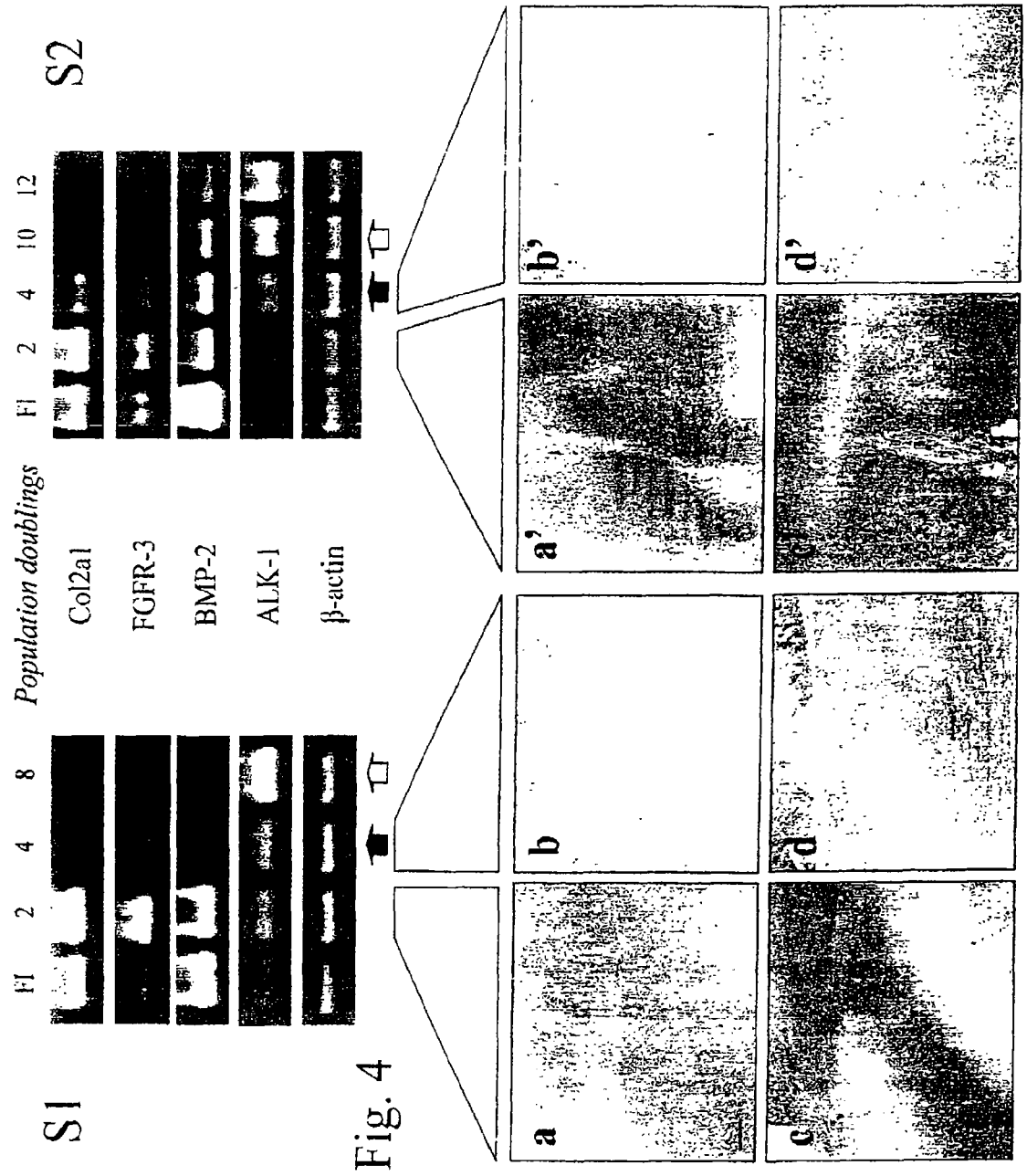
FIG. 4 is a set of pictures showing the molecular profile (by RT-PCR) of articular chondrocytes during in vitro expansion and the respective histology after 2 and 4 population duplications.

FIG. 4 shows that serial expansion of human adult articular chondrocytes results in the loss of their capacity to form cartilage in vivo. Samples from 2 independent donors (S1 and S2) were expanded. Upon passaging, aliquots of the cell suspension were injected in nude mice or used for gene expression analysis. After 2 population duplications, chondrocytes could still form mature cartilage tissue as evaluated by alcian blue (a and a') and safranin O (c and c'). After 4 population doublings—black arrow—the loss of cartilage forming ability was heralded by the formation of more immature implants as shown by alcian blue (b and b') and safranin O (d and d') stainings. Chondrocytes from further passages—open arrow—did not form any retrievable implant. The loss of the cartilage forming potential was marked by downregulation of type 2 collagen, Fgfr3, and Bmp2 mRNA, while the expression of Alk1 mRNA was upregulated. FI is freshly isolated chondrocytes. Scale bar is 200 µm. The appearance of the negative marker ALK-1 is associated with or heralds the state of non-formation of a retrievable implant and the appearance of this negative marker is associated with downregulation of the positive markers.

Figure 5:
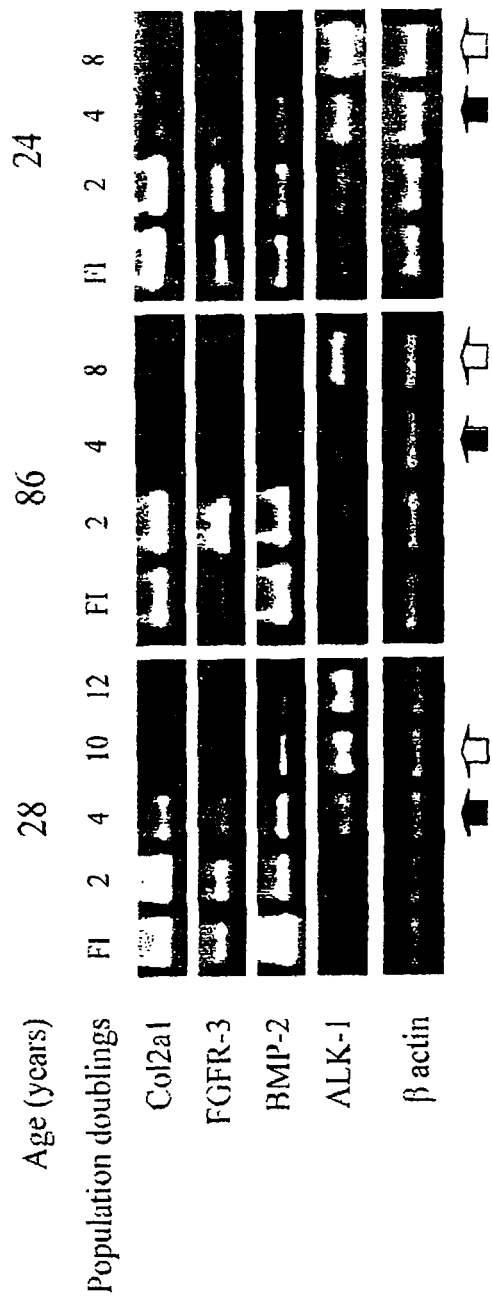
FIG. 5 is a set of pictures showing the molecular profile of articular chondrocytes from donors of different ages during in vitro expansion.

FIG. 5 shows that the set of molecular markers predict the capacity of AHAC to form stable cartilage in vivo independently on the donor age. Freshly isolated (FI) and serially passaged chondrocytes from donors of different ages (range 28-86 yr old) were challenged in our in vivo assay throughout expansion. The black arrow marks the passage when a decline of the maturity of the implant was first detected. The open arrow marks the first passage from which no implant could be retrieved. Again the downregulation of the positive markers is followed by upregulation of the negative marker ALK-1 and, at the same time, the appearance of ALK-1 heralds the stage at which no implant can be retrieved.

Figure 6:
FIG. 6 is a set of pictures (B) showing the results of RT-PCR analysis for various molecular markers in articular chondrocytes throughout passaging and in passaged chondrocytes that had been challenged with the agarose assay. The figure also shows a picture of chondrocytes cultured in low melting agarose (A).
Figure 6:
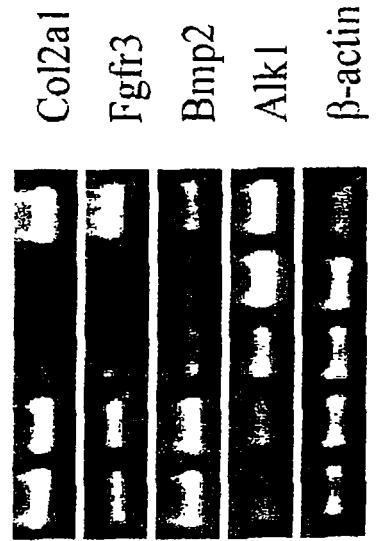

FIG. 6 shows that the agarose assay does not predict the cartilage tissue forming ability of expanded chondrocytes in our in vivo assay. Freshly isolated (FI) and serially passaged adult human articular chondrocytes were injected in nude mice and tested in the agarose assay. (a) Although the cells lost their in vivo cartilage tissue forming ability after the second passage, they could still grow in anchorage independent conditions in agarose after passage 5 (about 10 population duplications). (b) The molecular profile of the same chondrocytes throughout passaging and after agarose culture is shown at A(10). FI stands for freshly isolated chondrocytes. The arrow indicates the first passage from which no implant could be retrieved. Although there has been rescue of the positive markers the negative marker was still upregulated and these cells did not form cartilage in vivo. This is a clear demonstration that positive marker presence, e.g. FGFR3, is indicative of healthy cartilage but is not necessarily exclusively indicative thereof. Hence, the use of negative markers alone to sort or to use a combination of positive and negative markers are preferred embodiments of the present invention.

Example 5

Figure 7:
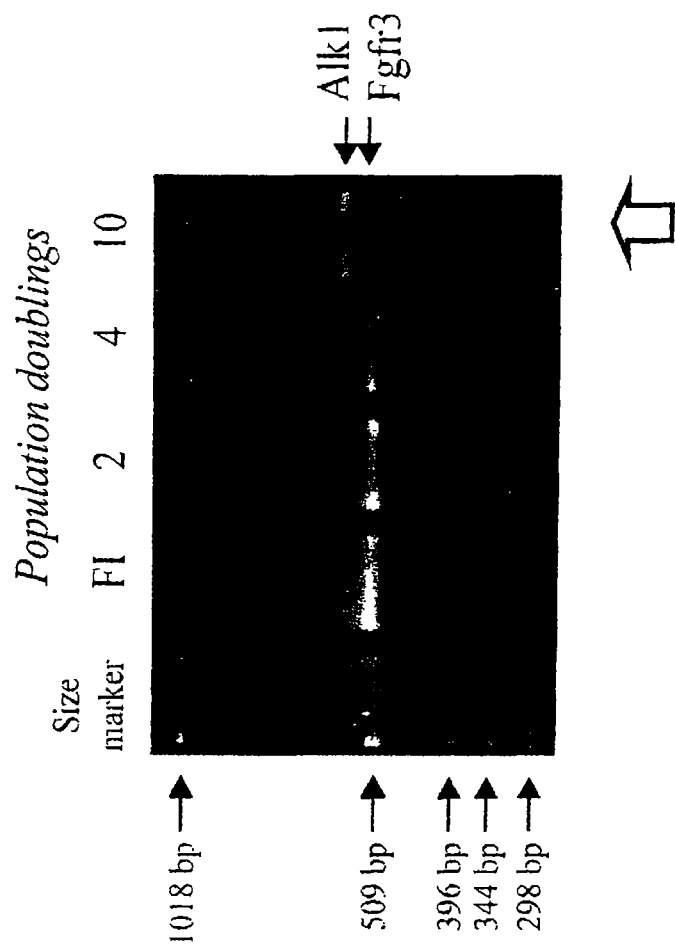
FIG. 7 is a picture showing RT-PCR analysis for Fgfr3 and Alk1 performed in the same tube of chondrocytes throughout in vitro passaging.

FIG. 7 shows that the presence of a negative marker for chondrocyte stability offers the possibility of an internal control for expression levels. RT-PCR for FGFR3 and Alk1 in the same tube is performed from freshly isolated (FI) and expanded chondrocytes at different passages. The appearance of the higher band corresponding to Alk1 and the decrease of the Fgfr3 band marks the loss of the capability to organize a cartilage implant in vivo. The arrow indicates the first passage from which no implant could be retrieved. This is coincident with the appearance of the negative marker ALK-1 and disappearance of the positive marker FGFR3.

Example 6

The In Vivo Assay and the Set of Markers for Predicting the Outcome of Autologous Chondrocyte Transplantation (ACT) in an Animal Model Male young New Zealand white rabbits or goats are used as a model of ACT Articular cartilage of the patella or femoral condyles are carved with a device producing a superficial cartilage defect 0.3 mm deep and 3 mm large in diameter, therefore not penetrating the underlying bone. Human articular chondrocytes are expanded to various extents as disclosed in example 1, analysed for the presence of markers associated with chondrocytic stability according to example 4 and injected back in the cartilage lesion under the periosteal flap as described by Brittberg et al. (1996) *Clin. Orthop.* (326): 270-83. After three months the animals are sacrificed and the joint surface defect analysed and scored by histology for the extent and quality of cartilage repair and for integration of the margins. In situ hybridisation for human Alu repeats is carried out in order to investigate the contribution of injected chondrocytes to the cartilage repair.

In a different approach we have devised an ex vivo model of JSD repair by ACT. The whole patella was excised from a male young New Zealand white rabbit, a cartilage defect was generated and previously isolated chondrocytes were injected underneath a periosteal flap sutured to cover the lesion. The patella was then placed in culture in DMEM supplemented with 10% FBS and antibiotic-antimycotic solution at 37° C. in 5% $CO_2$ atmosphere. After 2 weeks the patella was fixed in 4% formaldehyde, imbedded in paraffin and analysed for histology and other techniques.

This setting allows tighter and more controlled experimental conditions and also a closer and much more flexible monitoring of the healing process by means of e.g. cell labelling, time point biopsy of the healing tissue for histologic and molecular analysis etc.

Example 7

Rescue of Serially Passaged Articular Chondrocytes

A short treatment with a growth factor from the TGF-β superfamily just before implantation can partially rescue serially passaged articular chondrocytes that have just lost phenotypic stability or reduce dramatically the cell expansion procedure occurring before cells can be injected for joint surface defects repair, ideally eliminating the need of it. The treatment is administered to cells in suspension for a short time and is followed by extensive washes in PBS just before injection. Similarly treated cells are tested for the expression of molecular markers linked to phenotypic stability of the articular chondrocyte.

Figure 8:
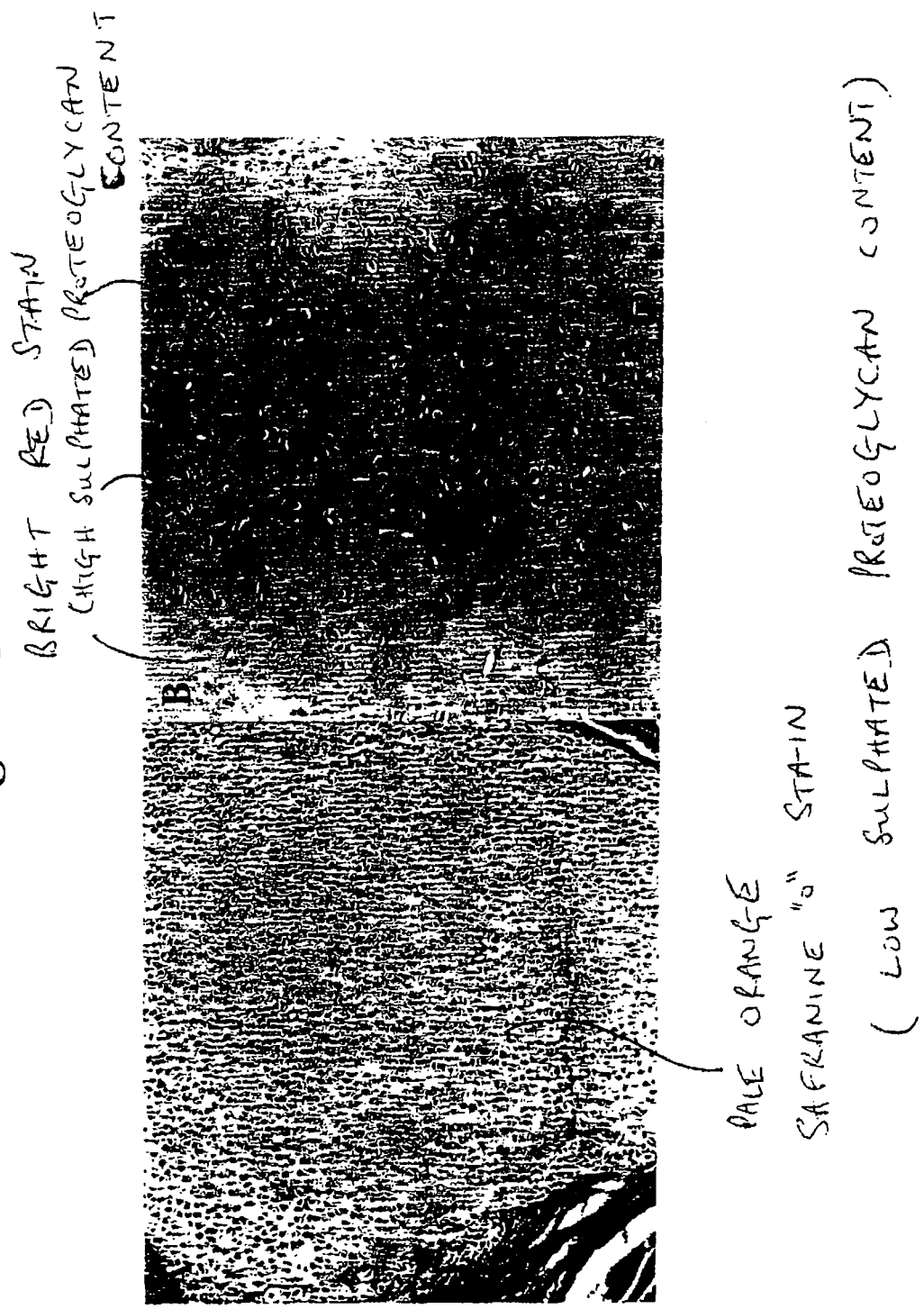
FIG. 8 is a set of two pictures showing implants obtained by injecting chondrocytes previously treated with or without CDMP1.

In a set of experiments, freshly isolated articular chondrocytes in single cell suspension were exposed for 30 minutes to 100 ng/ml of CDMP-1 in Nutrient Mixture Ham's F-12 (Life Technologies) at 37° C., washed twice in PBS and injected in the in vivo assay of example 2. Control injections were made with chondrocytes exposed to HAM-F12 alone. After 3 weeks cartilage implants were weighed, digested in 0.2% crude collagenase at 37° C. and isolated cells were counted. The implant obtained from CDMP-1 treated cells had a wet weight three times higher as compared to samples treated with HAM-F12 alone, and cell count was twice as high. As shown in FIG. 8, also the production of highly sulphated proteoglycans was enhanced as witnessed by a more intense metachromatic staining with Safranin O in the implant obtained from CDMP-1 treated chondrocytes (FIG. 8B) as compared to control (FIG. 8A). This shows that a short exposure to CDMP-1 in suspension, just before injection, is capable of enhancing the chondrocytic phenotype as measured by the in vivo assay of example 2. Furthermore, the effectiveness of such short pulse makes prolonged, expensive and potentially dangerous expansions unnecessary.

Example 8

Isolation of Stable Chondrocytes from a Mixed Cell Population by the Use of Flow-Cytometry During cell expansion, as demonstrated in example 4, some chondrocytes become phenotypically unstable and unable to organise cartilage tissue in vivo. As a consequence, the chondrogenic potential of an expanded chondrocyte population depends not only from the mere number of cells but also from the number of phenotypically stable chondrocytes that it contains. The identification of membrane-associated molecular markers for both stable and unstable chondrocytes—for instance FGFR-3 and ALK-1 respectively or any markers co-detectable therewith—gives the opportunity to select optimal cells for ACT. The entire expanded cell population is incubated with antibodies directed to ALK-1 and/or FGFR-3, or any membrane-markers co-detectable therewith, labelled with different fluorochromes. FACS analysis on double-labelled or multi-labelled cells depicts the distribution of stable and unstable chondrocytes within the total pool. If needed, cell sorting is used to separate the stable from the unstable chondrocytes (e.g. using positive markers) or to sort the unstable from the stable (e.g. using negative markers). A small aliquot of the sorted stable chondrocyte population is used for quality control using, for example, other independent positive and negative markers of chondrocyte stability (e.g. type II collagen and BMP-2 as positive markers and collagen type X as negative marker). The remaining stable chondrocytes are recovered in culture medium containing autologous serum and prepared for ACT. This allows obtaining a cell suspension composed of a consistent number of stable chondrocytes, suitable for implantation or for use in a pharmaceutical composition, all or a majority of the cells contributing to cartilage repair and not being a mixture of heterogeneous cells regardless of their phenotype. It also allows eliminating from the pool unstable chondrocytes that not only are unable to generate cartilage in vivo but can potentially hamper the appropriate repair.

Example 9

Figure 9:
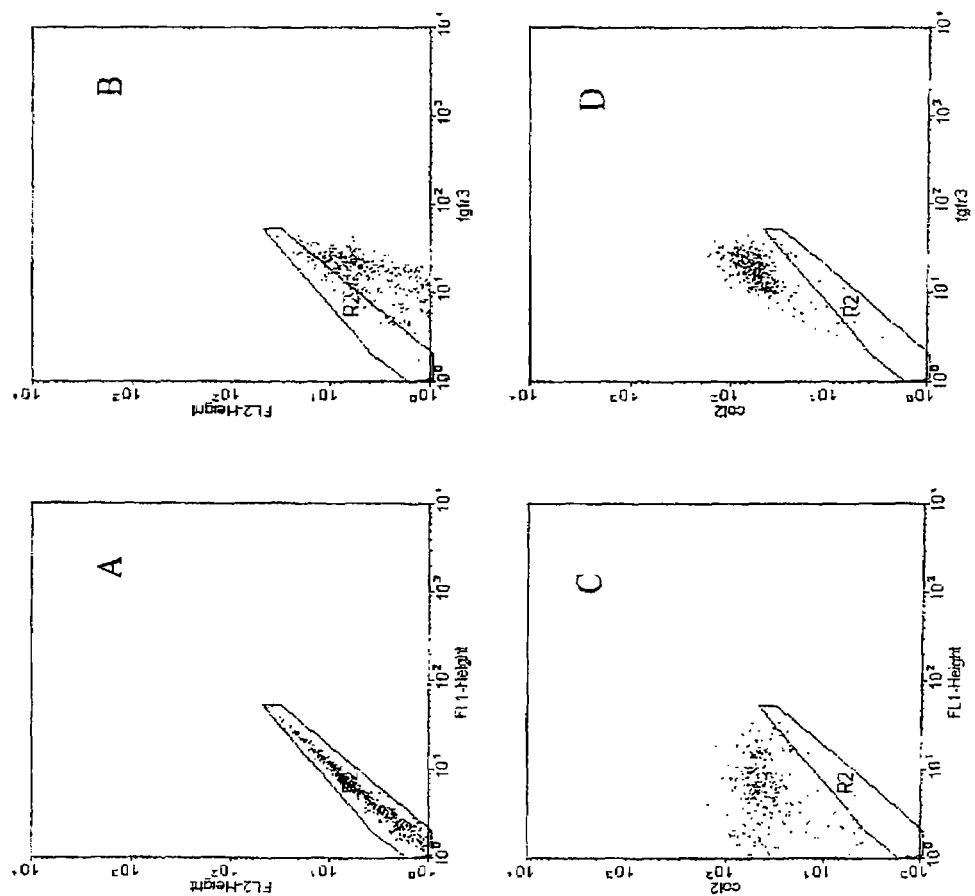
FIG. 9 is a set of four graphs obtained by flow-cytometric analysis, (a) unlabeled, (b) labelled with rabbit human FGFR3 antibody, (c) labelled with mouse anti-human collagen type 2 antibody and (d) with both antibodies.

FIG. 9 shows that most cells isolated from human adult articular cartilage co-express type 2 collagen and FGFR3 simultaneously. Cells were released from cartilage tissue by enzymatic digestion in 0.2% collagenase overnight, permeabilized using Fix&Pem reagent (Sigma) and either left unlabeled (A) or labeled with rabbit anti-human FGFR3 antibody (B), or labeled with mouse anti-human collagen type 2 antibody (C) or labeled with both of these (D). Fluorescein or phycoerytrin conjugated antibodies to, respectively, rabbit or mouse IgG were used as secondary antibodies. Flow-cytometric analysis shows that 80% of the cells are positive for FGFR3 (in B) and 85% of the cells for collagen type 2 (in C). Panel D shows that individual cells are co-expressing both FGFR3 and collagen type 2 indicating that FGFR3 is present in fully differentiated cells and is not a marker for skeletal precursor cells.

Example 10

The present invention also includes cells and cell cultures which express positive and negative markers described above in specific ratios. Due to commercial, practical and time restraints it is not always possible to carry out the cell sorting methods described above such that every cell expresses positive markers and does not express negative markers.

In order to determine the ratio of cells with positive markers (Cell$^+$) to those with negative markers (Cell$^-$) the in vivo assay and diagnostic methods described above have been used on human cell populations to determine when a satisfactory implant can be expected, i.e. that the implant will produce healthy stable cartilage. These experiments show that when the ratio Cell$^+$/Cell$^-$ is 1 or above suitable implants may be prepared from such a cell population. Preferably, the ratio is 2 or more. A ratio of 5 or more is considered to provide a significant security of a successful implant. The ratio may be advantageously obtained from examination of the DNA chips described above.

What is claimed is:

1. A method of treating a connective tissue defect in a patient comprising the step of transplanting chondrocytes to a connective tissue site in a patient, using passaged chondrocytes that have been prepared using the method steps of:
   a) providing articular cartilage from said patient
   b) isolating chondrocytes from said articular cartilage by enzymatic digestion
   c) expanding said isolated chondrocytes by serial passaging,
   d1) detecting in said passaged chondrocytes the expression of bone morphogenic protein-2(BMP-2), fibroblast growth factor receptor 3 (FGFR-3), or Collagen type II, or
   d2) detecting in said passaged chondrocytes the expression of activin-like kinase-1 (ALK-1) or Collagen type X
   e) selecting a cell population of passaged chondrocytes wherein a cell population that has either (1) expression of BMP-2, FGR-3 or collagen type II or has (2) no expression of Collagen Type X or no expression of ALK-1 is selected,
   f) transplanting said cell population to a connective tissue site in said patient.

2. The method according to claim 1, wherein said expression is detected by means of a monoclonal or polyclonal antibody against a negative or positive marker.

3. The method according to claim 1, further comprising the step seeding a prosthetic device intended to be anchored into a mammal with said selected cell population.

\* \* \* \* \*

SEQUENCE LISTING

<160> NUMBER OF SEQ ID NOS: 1

<210> SEQ ID NO 1
<211> LENGTH: 40
<212> TYPE: PRT
<213> ORGANISM: Homo sapiens

<400> SEQUENCE: 1

Thr Gly Leu Val Pro Ser Glu Arg Val Leu Val Gly Pro Gln Arg Leu
1               5                   10                  15

Gln Val Leu Asn Ala Ser His Glu Asp Ser Gly Ala Tyr Ser Cys Arg
            20                  25                  30

Gln Arg Leu Thr Gln Arg Val Leu
        35                  40